(12) United States Patent
Angbrant et al.

(10) Patent No.: US 8,138,333 B2
(45) Date of Patent: Mar. 20, 2012

(54) SULFONYL-INDOLE DERIVATIVES

(75) Inventors: Johan Angbrant, Uppsala (SE); Peter Brandt, Uppsala (SE); Rune Ringom, Uppsala (SE); Bengt Lindqvist, Uppsala (SE)

(73) Assignee: Proximagen Limited, London (GB)

( * ) Notice: Subject to any disclaimer, the term of this patent is extended or adjusted under 35 U.S.C. 154(b) by 1012 days.

(21) Appl. No.: 12/075,979

(22) Filed: Mar. 13, 2008

(65) Prior Publication Data

US 2008/0293694 A1    Nov. 27, 2008

Related U.S. Application Data

(60) Provisional application No. 61/002,029, filed on Nov. 5, 2007.

(30) Foreign Application Priority Data

Mar. 13, 2007  (SE) ...................... 0700611

(51) Int. Cl.
C07D 471/06 (2006.01)
C07D 487/06 (2006.01)
(52) U.S. Cl. .......................... 540/577; 546/84
(58) Field of Classification Search .................. None
See application file for complete search history.

(56) References Cited

U.S. PATENT DOCUMENTS

| | | | |
|---|---|---|---|
| 3,833,591 A | 9/1974 | McManus |
| 3,950,343 A | 4/1976 | Phillip et al. |
| 6,133,287 A | 10/2000 | Slassi et al. |
| 2003/0229069 A1 | 12/2003 | Clarke et al. |

FOREIGN PATENT DOCUMENTS

| | | |
|---|---|---|
| GB | 2341549 A | 3/2000 |
| WO | WO-9603400 A1 | 2/1996 |
| WO | WO-0034242 A1 | 6/2000 |
| WO | WO-02/32863 A1 | 4/2002 |

OTHER PUBLICATIONS

Vippagunta et al., Crystalline solids, 48 Adv. Drug Delivery Rev. 3-26 (2001).*
Liu et al., A regiospecific synthesis of a series of 1-sulfonyl azepinoindoles as potent 5-HT6 ligands, 18 Bioorg. & Med. Chem. Letts., 3929-3931 (2008).*
Russell et al., "$N$-Arylsulfonylindole Derivatives as Serotonin 5-HT$_6$ Receptor", J.Med.Chem. 2001, vol. 44, p. 3881-3895.
Doddareddy et al., "CoMFA and CoMSIA 3D QSAR analysis on $N_1$-arylsulfonylindole compounds as 5-HT$_6$ antagonists", Bioorganic & Medicinal Chemistry 2004, vol. 12, p. 3977-3985.
Cole et al., "$N_1$-arylsulfonyl-3-(1,2,3,6-tetrahydropyridin-4-yl)-1$H$—indole derivatives are potent and selective 5-HT$_6$ receptor antagonists", Bioorganic & Medicinal Chemistry Letters 2005, vol. 15, p. 379-383.
Pullagurla et al., "$N_1$-Benzensulfonylgramine and $N_1$-Benzensulfonylskatole: Novel 5-HT$_6$ Receptor Ligand Templates", Bioorganic & Medicinal Chemistry Letters 2003, vol. 13, p. 3355-3359.
Bowman et al., "1,3,4,5-Tetrahydrobenz[cd]indoles and Related Compounds", J. Chem. Society, Perkins Transactions 1, No. 15, 1972, p. 1926-1932.
Strekowski et al., "Synthesis of Analogs of the Ergot Alkaloids", J. Heterocyclic Chem., vol. 37, 2000, p. 1495-1499.
Yokoyama et al.,"Optically active total synthesis of clavicipitic acid", J. Organic Chemistry, vol. 60, 1995, p. 1486-1487.

* cited by examiner

*Primary Examiner* — Janet Andres
*Assistant Examiner* — Timothy R Rozof
(74) *Attorney, Agent, or Firm* — Edwards Wildman Palmer LLP; Jeffrey D. Hsi

(57) ABSTRACT

The present invention relates to novel compounds of formula (I):

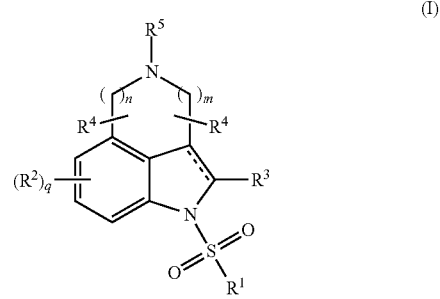

wherein $R^1$, $R^2$, $R^3$, $R^4$, and $R^5$ are as described herein, to pharmaceutical compositions comprising the compounds, to processes for their preparation, as well as to the use of the compounds for the preparation of a medicament against 5-HT$_6$ receptor-related disorders.

17 Claims, No Drawings

SULFONYL-INDOLE DERIVATIVES

CROSS REFERENCE TO RELATED APPLCIATIONS

This application claims priority to U.S. Provisional Patent Application No. 61/002,029 filed Nov. 5, 2007 and Sweden Patent Application No. 0700611-7, filed Mar. 13, 2007, the contents of each are hereby incorporated by reference in their entirety.

TECHNICAL FIELD

The present invention relates to novel compounds, to pharmaceutical compaositions comprising the compounds, to processes for their preparation, as well as to the use of the compounds for the preparation of a medicament against 5-$HT_6$ receptor-related disorders.

BACKGROUND OF THE INVENTION

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type 2 diabetes. Searching for compounds that reduce body weight has been going on for many decades. One line of research has been activation of serotoninergic systems, either by direct activation of serotonin receptor subtypes of by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and sepression. Multiple serotonin receptor subtypes have been identified and cloned. One of these, the 5-$HT_6$ receptor, was cloned by several groups in 1993 (Ruat, M. et al.(1993) Biochem. Biophys. Res. Commun. 193:268-276; Sebben, M. et al. (1994) NeuroReport 5:2553-2557). This receptor is positively coupled to adenylyl cyclase and displays affinity for antidepressants such as clozapine. The effect of 5-$HT_6$ antagonist and 5-$HT_6$ antisense oligonucleotides to reduce food intake in rats has been reported (Bentley, J.C. et al. (1999) Br J Pharmacol. Suppl. 126, P66; Bentley, J.C. et al. (1997) J. Psychopharmacol. Suppl. A64, 255; Woolley M.L. et al. (2001) Neuropharmacology 41:210-219).

Compounds with enhanced affinity and selectivity for the 5$HT_6$ receptor have been identified, e.g. in WO 00/34242 and by Isaac, M. et al. (2000) 6-Bicyclopiperazinyl-1-arylsulphonylindoles and 6-Bicyclopiperidinyl-1-arylsulphonylindoles derivatives as novel, potent and selective 5-$HT_6$ receptor antagonists. Bioorganic & Medicinal Chemistry Letters 10: 1719-1721 (2000), Bioorganic & Medicinal Chemistry Letters 13: 3355-3359 (2003), Expert Opinion Therapeutic Patents 12(4) 513-527 (2002).

DISCLOSURE OF THE INVENTION

It has surprisingly been found that the compounds according to the present invention show affinity for the 5-$HT_6$ receptor at nanomolar range. Compounds according to the present invention and their pharmaceutically acceptable salts have 5-$HT_6$ receptor antagonist, agonist and partial agonist activity, preferably antagonist activity, and are believed to be of potential use in the treatment or prophylaxis of obesity and type 2 diabetes, to achieve reduction of body weight and of body weight gain, as well as in the treatment or prophylaxis of disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea and/or schizophrenia, panic attacks, Attention Deficit Hyperactive Disorder (ADHD), withdrawal from drug abuse (e.g. abuse of amphetamine, cocaine abuse and/or nicotine), neurodegenerative diseases characterized by impaired neuronal growth, and pain. The reduction of body weight and of body weight gain (e.g. treating body-weight disorders) is achieved inter alia by reduction of food intake. As used herein, the term "body weight disorders" refers to the disorders caused by an imbalance between energy intake and energy expenditure, resulting in abnormal (e.g. excessive) body weight. Such body weight disorders include obesity.

One object of the present invention is a compound of the formula (I)

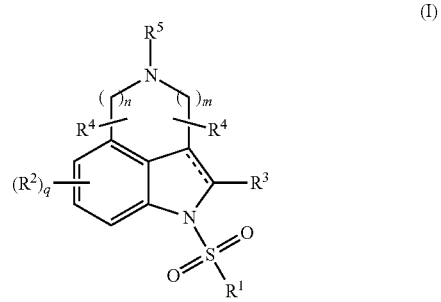

(I)

wherein:
 represents a single bond or a double bond;
m and n are each independently selected from 1, 2, and 3, provided that m+n≦4;
$R^1$ is a group selected from:
(a) $C_{1-6}$-alkyl,
(b) $C_{3-7}$-cycloalkyl,
(c) $C_{3-6}$-alkenyl,
(d) aryl,
(e) aryl-$C_{2-6}$-alkenyl,
(f) aryl-$C_{1-6}$-alkyl,
(g) heteroaryl,
(h) heteroaryl-$C_{2-6}$-alkenyl, and
(i) heteroaryl-$C_{1-6}$-alkyl,
wherein any heteroaryl or aryl residue, alone or as part of another group, is optionally independently substituted in one or more positions with a substituent selected from:
(a) halogen,
(b) $C_{1-6}$-alkyl,
(c) hydroxy-$C_{1-6}$-alkyl,
(d) fluoro-$C_{1-6}$-alkyl,
(e) $C_{3-7}$-cycloalkyl,
(f) hydroxy-$C_{3-7}$-cycloalkyl,
(g) fluoro-$C_{3-7}$-cycloalkyl,
(h) methyl-$C_{3-7}$-cycloalkyl,
(i) $C_{3-4}$-cycloalkyl-$C_{1-3}$-alkyl,
(j) $C_{3-4}$-cycloalkyl(hydroxy)-$C_{1-3}$-alkyl,
(k) $C_{1-6}$-alkoxy,
(l) fluoro-$C_{1-6}$-alkoxy,
(m) $C_{1-2}$-alkoxy-$C_{1-4}$-alkyl, (n) $C_{3-7}$-cycloalkoxy,
(o) fluoro-$C_{3-7}$-cycloalkoxy,
(p) methyl-$C_{3-7}$-cycloalkoxy,
(q) $C_{2-6}$-alkenyl,
(r) fluoro-$C_{2-6}$-alkenyl,
(s) $C_{2-6}$-alkynyl,
(t) hydroxy,
(u) —$SCF_3$,
(v) —$SCF_2H$,
(w) —$SO_2NR^6R^6$,
(x) —$S(O)_eR^7$, wherein e is 0, 1, 2 or 3,
(y) —$OSO_2R^7$,
(z) —CN,
(aa) —$NR^6R^6$,
(ab) —$NHSO_2R^7$,
(ac) —$NR^8COR^7$,
(ad) —$NO_2$,
(ae) —$CONR^6R^6$,
(af) —$COR^7$,
(ag) —COOH,
(ah) $C_{1-6}$-alkoxycarbonyl,
(ai) aryl,
(aj) heteroaryl,
(ak) aryloxy, and
(al) heteroaryloxy,
wherein any (ai) aryl or (aj) heteroaryl, alone or as part of another group, is optionally substituted in one or more positions with a substituent selected from:
(a) halogen,
(b) $C_{1-4}$-alkyl,
(c) $C_{1-4}$-alkoxy,
(d) —$CF_3$, and
(e) —CN;
q is selected from 0-3;
each $R^2$ is independently selected from:
(a) halogen,
(b) $C_{1-6}$-alkyl,
(c) hydroxy-$C_{1-6}$-alkyl,
(d) fluoro-$C_{1-6}$-alkyl,
(e) $C_{3-7}$-cycloalkyl,
(f) hydroxy-$C_{3-7}$-cycloalkyl,
(g) fluoro-$C_{3-7}$-cycloalkyl,
(h) methyl-$C_{3-7}$-cycloalkyl,
(i) $C_{3-4}$-cycloalkyl-$C_{1-3}$-alkyl,
j) $C_{3-4}$-cycloalkyl(hydroxy)-$C_{1-3}$-alkyl,
(k) $C_{1-6}$-alkoxy,
(l) fluoro-$C_{1-6}$-alkoxy,
(m) $C_{1-2}$-alkoxy-$C_{1-4}$-alkyl,
(n) $C_{3-7}$-cycloalkoxy,
(o) fluoro-$C_{3-7}$-cycloalkoxy,
(p) methyl-$C_{3-7}$-cycloalkoxy,
(q) $C_{2-6}$-alkenyl,
(r) fluoro-$C_{2-6}$-alkenyl,
(s) $C_{2-6}$-alkynyl,
(t) hydroxy,
(u) —$SCF_3$,
(v) —$SCF_2H$,
(w) —$SO_2NR^6R^6$,
(x) —$S(O)_eR^7$, wherein e is 0, 1, 2 or 3,
(Y) —$OSO_2R^7$
(z) —CN,
(aa) —$NR^6R^6$,
(ab) —$NHSO_2R^7$,
(ac) —$NR^8COR^7$,
(ad) —$NO_2$,
(ae) —$CONR^6R^6$,
(af) —$CO—R^7$,
(ag) —$OCONR^6R^6$,
(ah) —$CO—R^7$, and
(ai) —$O—CH_2$-aryl;
wherein any aryl residue is optionally substituted in one or more positions with a substituent selected from:
(a) halogen,
(b) $C_{1-4}$-alkyl,
(c) $C_{1-4}$-alkoxy,
(d) —$CF_3$, and
(e) —CN;
$R^3$ is a group selected from:
(a) hydrogen,
(b) $C_{1-6}$-alkyl,
(c) $C_{3-7}$-cycloalkyl,
(d) $C_{3-4}$-cycloalkyl-$C_{1-3}$-alkyl,
(e) hydroxy-$C_{1-4}$-alkyl
(f) hydroxy-$C_{3-7}$-cycloalkyl,
(g) $C_{3-4}$-cycloalkyl(hydroxy)-$C_{1-3}$-alkyl,
(h) $C_{1-2}$-alkoxy-$C_{1-4}$-alkyl,
(i) —$COOR^8$,
(j) —$CONR^6R^6$,
(k) —$CO—R^7$,
(l) —CN,
(m) halogen,
(n) aryl, and
(o) heteroaryl;
wherein any heteroaryl or aryl residue is optionally independently substituted in one or more positions with a substituent selected from:
(a) halogen,
(b) $C_{1-4}$-alkyl,
(c) $C_{1-4}$-alkoxy,
(d) —$CF_3$, and
(e) —CN;
each $R^4$ is independently selected from:
(a) hydrogen,
(b) $C_{1-4}$-alkyl,
(c) fluoro-$C_{1-4}$-alkyl,
(d) $C_{3-5}$-cycloalkyl,
(e) fluoro-$C_{3-5}$-cycloalkyl,
(f) $C_{3-5}$-cycloalkyl-methyl,
(g) hydroxy-$C_{1-4}$-alkyl,
(h) cyano;
(i) methoxy,
(j) hydroxy, and
(k) oxo,
provided that when $R^4$ is hydroxy or oxo, then either m or n is 2 or 3, and
$R^4$ is not attached on a carbon in alpha position to the ring nitrogen atom;
$R^5$ is a group selected from:
(a) hydrogen,
(b) $C_{1-4}$-alkyl,
(c) fluoro-$C_{1-4}$-alkyl,
(d) 2-cyanoethyl,
(e) hydroxy-$C_{2-4}$-alkyl,
(f) $C_{3-4}$-alkenyl,
(g) $C_{3-4}$-alkynyl,
(h) $C_{3-7}$-cycloalkyl,
(i) methyl-$C_{3-7}$-cycloalkyl
(j) fluoro-$C_{3-7}$-cycloalkyl,
(k) $C_{3-4}$-cycloalkyl-$C_{1-4}$-alkyl,
(l) $C_{1-4}$-alkoxy-$C_{2-4}$-alkyl,
(m) —$N(R^6)_2$—$C_{2-4}$-alkyl,
(n) imidazolyl-methyl, and
(o) pyrrolidinyl-methyl;

each R is a group independently selected from:
(a) hydrogen,
(b) $C_{1-6}$-alkyl,
(c) fluoro-$C_{2-6}$-alkyl, and
(d) $C_{3-7}$-cycloalkyl, or
two $R^6$ groups together with the nitrogen to which they are attached form a heterocyclic ring optionally substituted with methyl;
each $R^7$ is a group independently selected from:
(a) hydrogen,
(b) $C_{1-6}$-alkyl,
(c) fluoro-$C_{1-6}$-alkyl,
(d) $C_{3-7}$-cycloalkyl,
(e) methyl-$C_{3-7}$-cycloalkyl,
(f) $C_{3-4}$-cycloalkyl-$C_{1-3}$-alkyl,
(g) aryl, and
(h) heteroaryl,
wherein any heteroaryl or aryl residue is optionally independently substituted in one or more positions with a substituent selected from:
(a) halogen,
(b) $C_{1-4}$-alkyl,
(c) $C_{1-4}$-alkoxy,
(d) —$CF_3$, and
(e) —CN;
each $R^8$ is independently a group selected from:
(a) hydrogen,
(b) $C_{1-6}$-alkyl,
(c) fluoro-$C_{1-6}$-alkyl, and
(d) $C_{3-7}$-cycloalkyl,
or $R^7$ and $R^8$ together with the atoms to which they are attached form a lactam ring when present in the group $NR^8COR^7$, or $R^7$ and $R^8$ together with the atoms to which they are attached form a sultam ring when present in the group $NR^8SO_2R^7$, and
pharmaceutically acceptable salts, hydrates, solvates, geometrical isomers, tautomers, optical isomers, and prodrug forms thereof.

Preferred compounds of the Formula (I) include those wherein
---- represents a double bond.
Preferred compounds of the Formula (I) include those wherein m and n are each independently selected from 1 and 2, provided that m+n≦3.
Preferred compounds of the Formula (I) include those wherein $R^1$ is a group selected from:
(a) aryl, in particular phenyl
(b) heteroaryl, in particular furanyl, thienyl, isoxazolyl, imidazolyl, thiazolyl, pyridyl, imidazothiazolyl, benzofuranyl, dihydrobenzofuranyl, benzothienyl, benzothiazolyl,
wherein any heteroaryl or aryl residue is unsubstituted or independently substituted in one or more positions with a substituent selected from:
(a) halogen,
(b) $C_{1-6}$-alkyl, in particular $C_{1-4}$-alkyl,
(c) fluoro-$C_{1-6}$-alkyl, in particular fluoro-$C_{1-2}$-alkyl,
(d) $C_{1-6}$-alkoxy, in particular $C_{1-2}$-alkoxy,
(e) fluoro-$C_{1-6}$-alkoxy, in particular fluoro-$C_{1-2}$-alkoxy, and
(f) —CN.
Preferred compounds of the Formula (I) include those wherein q is 0, 1, or 2, and (when q is 1 or 2) each $R^2$ is independently a group selected from:
(a) halogen,
(b) $C_{1-2}$-alkyl,
(c) fluoro-$C_{1-2}$-alkyl,
(d) $C_{1-2}$-alkoxy,
(e) fluoro-$C_{1-2}$-alkoxy,
(f) hydroxy, and
(g) —O—$SO_2$—$CF_3$.
Preferred compounds of the Formula (I) include those wherein $R^3$ is a group selected from:
(a) hydrogen,
(b) $C_{1-2}$-alkyl,
(c) —F, and
(d) —Cl.
Preferred compounds of the Formula (I) include those wherein each $R^4$ is independently a group selected from:
(a) hydrogen,
(b) methyl, and
(c) oxo.
Preferred compounds of the Formula (I) include those wherein $R^5$ is a group selected from:
(a) hydrogen,
(b) $C_{1-3}$-alkyl,
(c) $N(R^6)_2$—$C_{2-4}$-alkyl-,
(d) imidazolyl-methyl, and
(e) pyrrolidinyl-methyl.
Preferred compounds of the Formula (I) include those wherein each $R^6$ is independently a group selected from:
(a) hydrogen, and
(b) methyl.
Preferred compounds of the Formula (I) include those wherein m+n=2.
Examples of preferred compounds wherein m+n=2 include compounds wherein
---- represents a double bond;
$R^1$ is a group selected from
(a) phenyl, or
(b) benzothienyl,
wherein phenyl is unsubstituted or independently substituted in one or two positions with a substituent selected from:
(a) trifluoromethyl,
(b) chloro,
(c) methyl, and
(d) methoxy;
q is 0;
$R^3$ and $R^4$ are hydrogen; and
$R^5$ is a group selected from:
(a) hydrogen,
(b) methyl,
(c) ethyl,
(d) dimethylaminoethyl,
(e) imidazol-2-yl-methyl, and
(f) pyrrolidinyl-methyl.
Specifically preferred compounds of the Formula (I), wherein m+n=2, are:
1-(phenylsulfonyl)-1,3,4,5-tetrahydropyrrolo[4,3,2-de]isoquinoline,
4-methyl-1-(phenylsulfonyl)-1,3,4,5-tetrahydropyrrolo[4,3,2-de]isoquinoline,
4-(1H-imidazol-2-ylmethyl)-1-(phenylsulfonyl)-1,3,4,5-tetrahydropyrrolo[4,3,2-de]isoquinoline,
N,N-dimethyl-2-[1-(phenylsulfonyl)-1,5-dihydropyrrolo[4,3,2-de]isoquinolin-4-(3H)-yl]ethanamine,
4-ethyl-1-(phenylsulfonyl)-1,3,4,5-tetrahydropyrrolo[4,3,2-de]isoquinoline,
1-(phenylsulfonyl)-4-(pyrrolidin-2-ylmethyl)-1,3,4,5-tetrahydropyrrolo[4,3,2-de]isoquinoline,
1-(phenylsulfonyl)-4-(pyrrolidin-3-ylmethyl)-1,3,4,5-tetrahydropyrrolo[4,3,2-de]isoquinoline, 1-[(2-chlorophenyl)sulfonyl]-4-ethyl-1,3,4,5-tetrahydropyrrolo[4,3,2-de]isoquinoline,
4-ethyl-1-{[2-(trifluoromethyl)phenyl]sulfonyl}-1,3,4,5-tetrahydropyrrolo[4,3,2-de]isoquinoline,
1-(1-benzothien-2-ylsulfonyl)-4-ethyl-1,3,4,5-tetrahydropyrrolo[4,3,2-de]isoquinoline, and
4-ethyl-1-[(2-methoxy-5-methylphenyl)sulfonyl]-1,3,4,5-tetrahydropyrrolo[4,3,2-de]isoquinoline.

Other preferred compounds of the Formula (I) include those wherein m+n=3.

Examples of preferred compounds wherein m+n=3 include compounds wherein
===== represents a double bond;
$R^1$ is a group selected from
  (a) phenyl,
  (b) furanyl,
  (c) thienyl,
  (d) isoxazolyl,
  (e) imidazolyl,
  (f) thiazolyl,
  (g) pyridyl,
  (h) imidazothiazolyl,
  (i) benzofuranyl,
  (j) dihydrobenzofuranyl,
  (k) benzothienyl, and
  (l) benzothiazolyl,
wherein $R^1$ is unsubstituted or independently substituted in one or more positions with a substituent selected from:
  (a) fluoro,
  (b) chloro,
  (c) bromo,
  (d) methyl,
  (e) ethyl,
  (f) n-propyl,
  (g) isopropyl,
  (h) tert-butyl,
  (i) trifluoromethyl,
  j) methoxy,
  (k) ethoxy, and
  (l) cyano;
q is 0 or 1;
each $R^2$ is independently a group selected from:
  (a) methoxy,
  (b) ethoxy,
  (c) hydroxy, and
  (d) —O—$SO_2$—$CF_3$;
$R^3$ is hydrogen;
each $R^4$ is independently a group selected from
  (a) hydrogen,
  (b) methyl, and
  (c) oxo,
  wherein at least one $R^4$ is hydrogen; and
$R^5$ is a group selected from
  (a) hydrogen,
  (b) methyl, and
  (c) ethyl.

More preferred compounds of the Formula (I) wherein m+n=3 are compounds wherein:
$R^1$ is a group selected from
  (a) phenyl, which may be unsubstituted or independently substituted in one or two positions with a substituent selected from: chloro, fluoro, methyl, ethyl, isopropyl, n-propyl, tert-butyl, methoxy, ethoxy, trifluoromethyl, and cyano;
  (b) thienyl, independently substituted in one or two positions with a substituent selected from chloro and methyl,
  (c) benzofuranyl,
  (d) bromo-dihydrobenzofuranyl,
  (e) benzothiazolyl,
  (f) imidazolyl, independently substituted in one or two positions with methyl,
  (g) chloroimidazothiazolyl,
  (h) benzothienyl, which may be unsubstituted or substituted in one or two positions with a substituent selected from chloro and methyl,
  (i) dimethylfuryl,
  (j) dimethylthiazolyl,
  (k) dimethylisoxazolyl, and
  (l) pyridinyl.

Specifically preferred compounds of the Formula (I) wherein m+n=3 are:
4-methyl-1-(phenylsulfonyl)-3,4,5,6-tetrahydro-1H-azepino[3,4,5-cd]indole,
4-ethyl-1-(phenylsulfonyl)-3,4,5,6-tetrahydro-1H-azepino[3,4,5-cd]indole,
1-(phenylsulfonyl)-3,4,5,6-tetrahydro-1H-azepino[5,4,3-cd]indole,
5-methyl-1-(phenylsulfonyl)-3,4,5,6-tetrahydro-1H-azepino[5,4,3-cd]indole,
1-(phenylsulfonyl)-3,4,5,6-tetrahydro-1H-azepino[3,4,5-cd]indole,
7-methoxy-6-methyl-1-(phenylsulfonyl)-3,4,5,6-tetrahydro-1H-azepino[5,4,3-cd]indole,
6-methyl-1-(phenylsulfonyl)-3,4,5,6-tetrahydro-1H-azepino[5,4,3-cd]indol-7-ol,
6-methyl-1-(phenylsulfonyl)-3,4,5,6-tetrahydro-1H-azepino[5,4,3-cd]indol-7-yl trifluoromethanesulfonate,
7-methoxy-5,6-dimethyl-1-(phenylsulfonyl)-3,4,5,6-tetrahydro-1H-azepino[5,4,3-cd]indole,
7-ethoxy-6-methyl-1-(phenylsulfonyl)-3,4,5,6-tetrahydro-1H-azepino[5,4,3-cd]indole,
1-[(2-chloro-6-methylphenyl)sulfonyl]-3,4,5,6-tetrahydro-1H-azepino[5,4,3-cd]indole,
1-[(3-chloro-2-methylphenyl)sulfonyl]-3,4,5,6-tetrahydro-1H-azepino[5,4,3-cd]indole,
1-[(3-chloro-4-fluorophenyl)sulfonyl]-3,4,5,6-tetrahydro-1H-azepino[5,4,3-cd]indole,
1-[(2-chlorophenyl)sulfonyl]-3,4,5,6-tetrahydro-1H-azepino[5,4,3-cd]indole,
1-[(3-chlorophenyl)sulfonyl]-3,4,5,6-tetrahydro-1H-azepino[5,4,3-cd]indole,
1-[(4-chlorophenyl)sulfonyl]-3,4,5,6-tetrahydro-1H-azepino[5,4,3-cd]indole,
1-[(3-fluorophenyl)sulfonyl]-3,4,5,6-tetrahydro-1H-azepino[5,4,3-cd]indole,
1-[(4-fluorophenyl)sulfonyl]-3,4,5,6-tetrahydro-1H-azepino[5,4,3-cd]indole,
1-[(2,6-difluorophenyl)sulfonyl]-3,4,5,6-tetrahydro-1H-azepino[5,4,3-cd]indole,
1-[(2,5-difluorophenyl)sulfonyl]-3,4,5,6-tetrahydro-1H-azepino[5,4,3-cd]indole,
1-[(3,5-difluorophenyl)sulfonyl]-3,4,5,6-tetrahydro-1H-azepino[5,4,3-cd]indole,
1-[(2,4-difluorophenyl)sulfonyl]-3,4,5,6-tetrahydro-1H-azepino[5,4,3-cd]indole,
1-[(3,4-difluorophenyl)sulfonyl]-3,4,5,6-tetrahydro-1H-azepino[5,4,3-cd]indole,
1-[(2-methylphenyl)sulfonyl]-3,4,5,6-tetrahydro-1H-azepino[5,4,3-cd]indole,
1-[(4-methylphenyl)sulfonyl]-3,4,5,6-tetrahydro-1H-azepino[5,4,3-cd]indole,
1-[(2,5-dimethyl-3-thienyl)sulfonyl]-3,4,5,6-tetrahydro-1H-azepino[5,4,3-cd]indole, 1-[(2,5-dimethylphenyl)sulfonyl]-3,4,5,6-tetrahydro-1H-azepino[5,4,3-cd]indole,
1-[(3,5-dimethylphenyl)sulfonyl]-3,4,5,6-tetrahydro-1H-azepino[5,4,3-cd]indole,
1-{[4-fluoro-3-(trifluoromethyl)phenyl]sulfonyl}-3,4,5,6-tetrahydro-1H-azepino[5,4,3-cd]indole,
1-(1-benzofuran-2-ylsulfonyl)-3,4,5,6-tetrahydro-1H-azepino[5,4,3-cd]indole,
1-(1,3-benzothiazol-6-ylsulfonyl)-3,4,5,6-tetrahydro-1H-azepino[5,4,3-cd]indole,
1-[(1-methyl-1H-imidazol-4-yl)sulfonyl]-3,4,5,6-tetrahydro-1H-azepino[5,4,3-cd]indole,
1-[(6-chloroimidazo[2,1-b][1,3]thiazol-5-yl)sulfonyl]-3,4,5,6-tetrahydro-1H-azepino[5,4,3-cd]indole,
1-{[2-(trifluoromethyl)phenyl]sulfonyl}-3,4,5,6-tetrahydro-1H-azepino[5,4,3-cd]indole,
1-(1-benzothien-2-ylsulfonyl)-3,4,5,6-tetrahydro-1H-azepino[5,4,3-cd]indole,
1-[(5-fluoro-2-methylphenyl)sulfonyl]-3,4,5,6-tetrahydro-1H-azepino[5,4,3-cd]indole,
1-{[3-(trifluoromethyl)phenyl]sulfonyl}-3,4,5,6-tetrahydro-1H-azepino[5,4,3-cd]indole,
1-{[4-(trifluoromethyl)phenyl]sulfonyl}-3,4,5,6-tetrahydro-1H-azepino[5,4,3-cd]indole,
4-methyl-2-(3,4,5,6-tetrahydro-1H-azepino[5,4,3-cd]indol-1-ylsulfonyl)benzonitrile,
1-[(4,5-dichloro-2-thienyl)sulfonyl]-3,4,5,6-tetrahydro-1H-azepino[5,4,3-cd]indole,
1-[(4-tert-butylphenyl)sulfonyl]-3,4,5,6-tetrahydro-1H-azepino[5,4,3-cd]indole,
1-[(2,5-dimethyl-3-furyl)sulfonyl]-3,4,5,6-tetrahydro-1H-azepino[5,4,3-cd]indole,
1-[(2,4-dimethyl-1,3-thiazol-5-yl)sulfonyl]-3,4,5,6-tetrahydro-1H-azepino[5,4,3-cd]indole,
1-[(3,5-dimethylisoxazol-4-yl)sulfonyl]-3,4,5,6-tetrahydro-1H-azepino[5,4,3-cd]indole,
1-[(5-chloro-2-thienyl)sulfonyl]-3,4,5,6-tetrahydro-1H-azepino[5,4,3-cd]indole,
4-(3,4,5,6-tetrahydro-1H-azepino[5,4,3-cd]indol-1-ylsulfonyl)benzonitrile,
3-(3,4,5,6-tetrahydro-1H-azepino[5,4,3-cd]indol-1-ylsulfonyl)benzonitrile,
1-[(4-methoxyphenyl)sulfonyl]-3,4,5,6-tetrahydro-1H-azepino[5,4,3-cd]indole,
1-[(2-methoxy-6-methylphenyl)sulfonyl]-3,4,5,6-tetrahydro-1H-azepino[5,4,3-cd]indole,
1-[(2-methoxy-5-methylphenyl)sulfonyl]-3,4,5,6-tetrahydro-1H-azepino[5,4,3-cd]indole,
1-[(2-methoxy-4-methylphenyl)sulfonyl]-3,4,5,6-tetrahydro-1H-azepino[5,4,3-cd]indole,
1-(1-benzothien-3-ylsulfonyl)-3,4,5,6-tetrahydro-1H-azepino[5,4,3-cd]indole,
1-[(4-isopropylphenyl)sulfonyl]-3,4,5,6-tetrahydro-1H-azepino[5,4,3-cd]indole,
1-[(4-propylphenyl)sulfonyl]-3,4,5,6-tetrahydro-1H-azepino[5,4,3-cd]indole,
1-[(5-ethyl-2-methoxyphenyl)sulfonyl]-3,4,5,6-tetrahydro-1H-azepino[5,4,3-cd]indole,
1-[(5-bromo-2,3-dihydro-1-benzofuran-7-yl)sulfonyl]-3,4,5,6-tetrahydro-1H-azepino[5,4,3-cd]indole,
1-[(5-chloro-3-methyl-1-benzothien-2-yl)sulfonyl]-3,4,5,6-tetrahydro-1H-azepino[5,4,3-cd]indole,
1-[(2-ethoxy-5-isopropylphenyl)sulfonyl]-3,4,5,6-tetrahydro-1H-azepino[5,4,3-cd]indole,
6-methyl-1-(phenylsulfonyl)-3,4,5,6-tetrahydro-1H-azepino[5,4,3-cd]indole,
1-(phenylsulfonyl)-1,4,5,6-tetrahydro-3H-azepino[5,4,3-cd]indol-3-one,
1-[(1,2-dimethyl-1H-imidazol-4-yl)sulfonyl]-3,4,5,6-tetrahydro-1H-azepino[5,4,3-cd]indole,
2-fluoro-5-(3,4,5,6-tetrahydro-1H-azepino[5,4,3-cd]indol-1-ylsulfonyl)benzonitrile,
1-(pyridin-3-ylsulfonyl)-3,4,5,6-tetrahydro-1H-azepino[5,4,3-cd]indole, and
1-(phenylsulfonyl)-3,4,5,6-tetrahydro-1H-azepino[5,4,3-cd]indol-3-ol.

The compounds of Formula (I) may be agonists, partial agonists or antagonists for the 5-HT$_6$ receptor. Preferably, the compounds act as partial agonists or antagonists for the 5-HT$_6$ receptor. More preferably the compounds act as antagonists for the 5-HT$_6$ receptor. The term "partial agonist of the 5-HT$_6$ receptor" means a compound which binds to the human 5-HT$_6$ receptor and do not fully antagonize 5-HT-induced cAMP formation in the intrinsic activity assay described herein (see "Biological Tests").

Another object of the present invention is a compound of Formula (I) for use in therapy, especially for use in the treatment or prophylaxis of a 5-HT$_6$ receptor-related disorder.

Examples of 5-HT$_6$ receptor-related disorders include: obesity, type II diabetes, disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse (e.g. abuse of cocaine, amphetamine and/or nicotine), neurodegenerative diseases characterized by impaired neuronal growth, and pain.

Another object of the present invention is a pharmaceutical formulation comprising a compound of Formula (I) as active ingredient, in combination with a pharmaceutically acceptable diluent or carrier, especially for use in the treatment or prophylaxis of a 5-HT$_6$ receptor-related disorder.

Another object of the present invention is a method for treating a human or animal subject suffering from a 5-HT$_6$ receptor-related disorder. The method can include administering to a subject (e.g., a human or an animal, dog, cat, horse, cow) in need thereof an effective amount of one or more compounds of Formula (I), their salts, or compositions containing the compounds or salts.

Another object of the present invention is a method for reducing body weight or reducing body weight gain. The method comprises administering to a subject in need thereof an effective amount of a compound of the Formula (I).

The methods delineated herein can also include the step of identifying that the subject is in need of treatment of the 5-HT$_6$ receptor-related disorder. Identifying a subject in need of such treatment can be in the judgment of a subject or a health care professional and can be subjective (e.g., opinion) or objective (e.g., measurable by a test or diagnostic method).

Another object of the present invention is a cosmetic composition comprising a compound as mentioned above as active ingredient, in combination with a cosmetically acceptable diluent or carrier, to achieve reduction of body weight and/or of body weight gain.

Another object of the present invention is a process for the preparation of a compound according to formula (I) of the invention comprising the following steps:

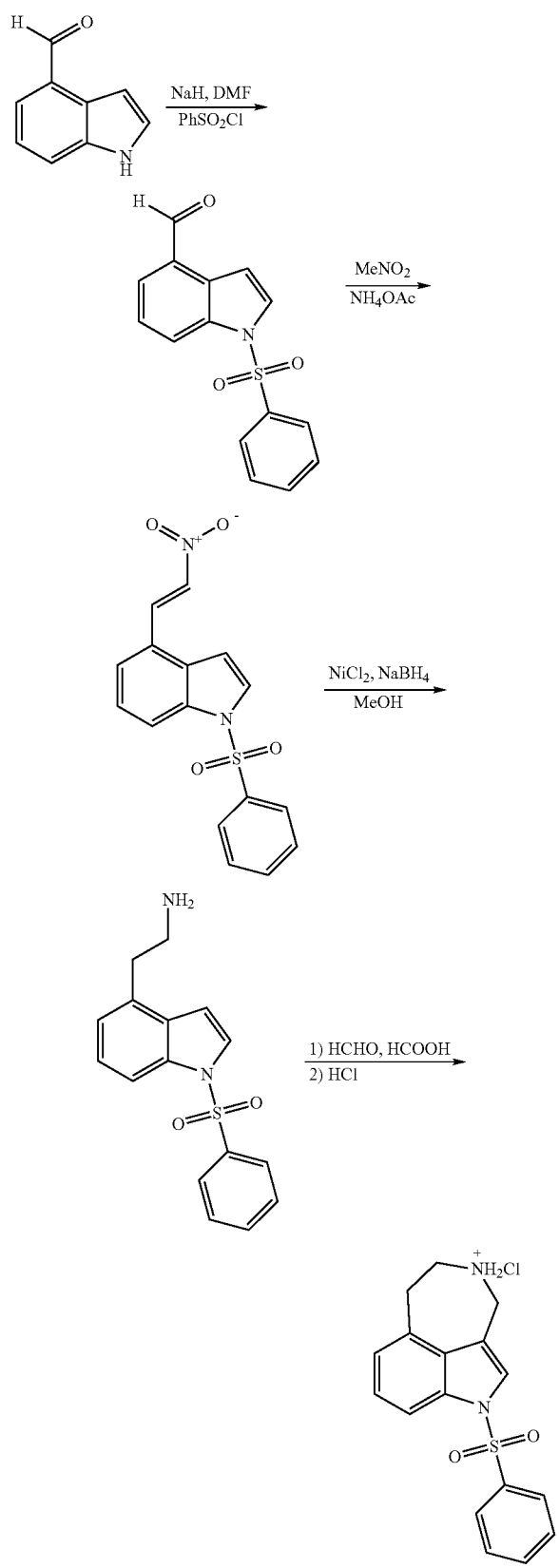

and optionally thereafter forming a pharmaceutically acceptable salt of the compound of formula (I).

Another object of the present invention is a process for the preparation of a compound according to formula (I) of the invention comprising the following steps:

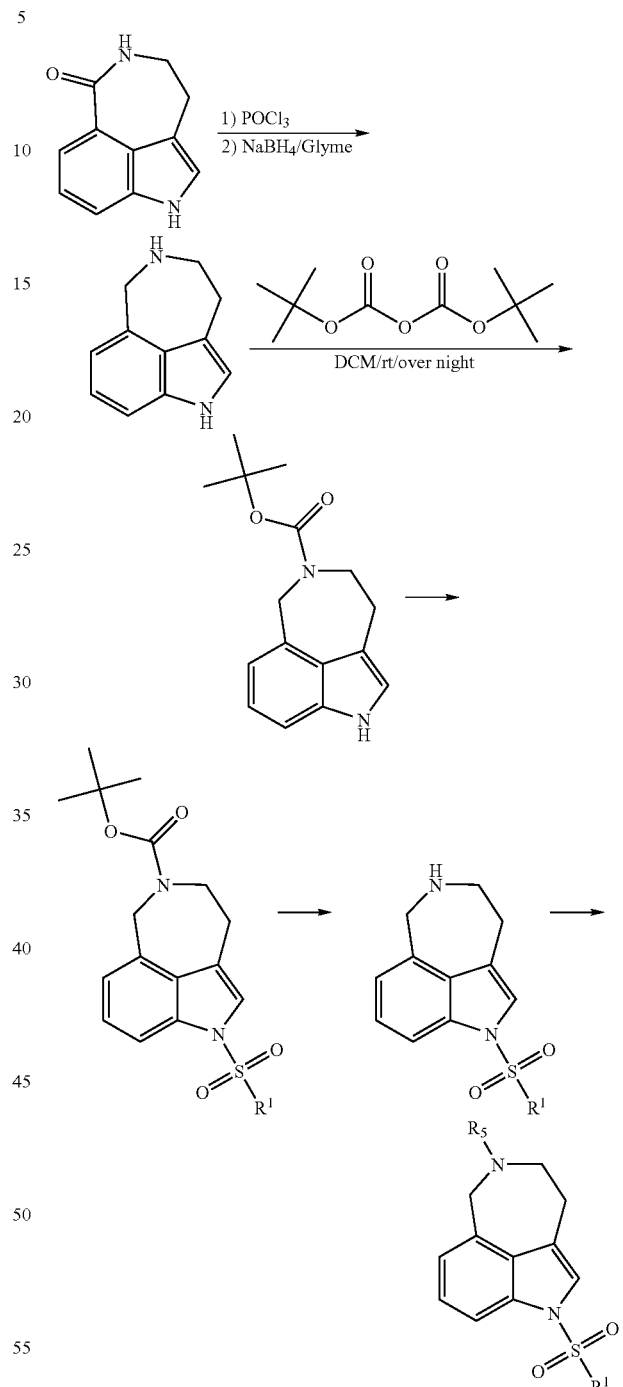

and optionally thereafter forming a pharmaceutically acceptable salt of the compound of formula (I).

Methods for carrying out the reactions described above are well known to those skilled in the art and/or are illustrated herein.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds.

In addition, various synthetic steps may be performed in an alternate sequence or order to give the desired compounds. Synthetic chemistry transformations useful in synthesizing applicable compounds are known in the art and include, for example, those described in R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The chemical structures in the schemes herein depict variables that are hereby defined commensurately with chemical groups (moieties, atoms, etc.) of the corresponding position in the compound formulae herein, whether identified by the same variable name (e.g., any R group ($R_1$, $R_2$, etc.)) or not. The suitability of a chemical group in a compound structure for use in synthesis of another compound structure is within the knowledge of one of ordinary skill in the art.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns. All isomeric forms possible (pure enantiomers, diastereomers, tautomers, racemic mixtures and unequal mixtures of two enantiomers) for the compounds delineated are within the scope of the invention. When the compounds described herein contain olefinic double bonds of geometric asymmetry, it is intended to include both trans and cis (E and Z) geometric isomers.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parentral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Definitions

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Likewise, "aryl-$C_{1-6}$-alkyl" means a $C_{1-6}$-alkyl group substituted by an aryl group. Examples include benzyl, 2-phenylethyl, 1-phenylethyl and 1-naphthylmethyl.

Unless otherwise stated, "fluoro-$C_{1-6}$-alkyl" means a $C_{1-6}$-alkyl group substituted by one or more fluorine atoms. Examples of said fluoro-$C_{1-6}$-alkyl include 2-fluoroethyl, fluoromethyl, trifluoromethyl and 2,2,2-trifluoroethyl.

Unless otherwise stated or indicated, the term "hydroxy-$C_{1-4}$-alkyl" denotes a straight or branched alkyl group that has a hydrogen atom thereof replaced with OH. Examples of said hydroxy-$C_{1-4}$-alkyl include hydroxymethyl, 2-hydroxyethyl, 2-hydroxypropyl and 2-hydroxy-2-methylpropyl.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

Unless otherwise stated or indicated, "fluoro-$C_{1-6}$-alkoxy" means a $C_{1-6}$-alkoxy group substituted by one or more fluorine atoms. Examples of said fluoro-$C_{1-6}$-alkoxy include trifluoromethoxy, difluoromethoxy, monofluoromethoxy, 2-fluoroethoxy, 2,2,2-trifluoroethoxy, and 1,1,2,2-tetrafluoroethoxy.

Unless otherwise stated or indicated, the term "$C_{1-4}$-alkoxy-$C_{2-4}$-alkyl" denotes a straight or branched alkoxy group having from 1 to 4 carbon atoms connected to an alkyl group having from 1 to 4 carbon atoms. Examples of said $C_{1-4}$-alkoxy-$C_{2-4}$-alkyl include methoxymethyl, ethoxymethyl, iso-propoxymethyl, n-butoxymethyl, and t-butoxymethyl. For parts of the range "$C_{1-4}$-alkoxy-$C_{2-4}$-alkyl" all subgroups thereof are contemplated such as $C_{1-3}$-alkoxy-$C_{2-4}$-alkyl, $C_{1-4}$-alkoxy-$C_{2-3}$-alkyl, $C_{1-2}$-alkoxy-$C_{2-3}$-alkyl, $C_{2-4}$-alkoxy-$C_{2-4}$-alkyl, $C_{2-3}$-alkoxy-$C_{2-4}$-alkyl, $C_{2-4}$-alkoxy-$C_{2-3}$-alkyl, etc.

Unless otherwise stated or indicated, the term "$C_{2-6}$-alkenyl" denotes a straight or branched alkenyl group having from 2 to 6 carbon atoms. Examples of said $C_{2-6}$-alkenyl include vinyl, allyl, 2,3-dimethylallyl, 1-butenyl, 1-pentenyl, and 1-hexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc. Likewise, "aryl-$C_{2-6}$-alkenyl" means a $C_{2-6}$-alkenyl group substituted by an aryl group. Examples of said aryl-$C_{2-6}$-alkenyl include styryl and cinnamyl.

Unless otherwise stated or indicated, the term "fluoro-$C_{2-6}$-alkenyl" denotes a straight or branched alkenyl group having from 2 to 6 carbon atoms substituted by one or more fluorine atoms. Examples of said fluoro-$C_{2-6}$-alkenyl include 1-fluorovinyl, 1,2-difluorovinyl, trifluorovinyl, and 2-fluoro-2-propen-1-yl.

Unless otherwise stated or indicated, the term "$C_{3-4}$-alkynyl" denotes a straight or branched alkynyl group having from 3 to 4 carbon atoms. Examples of said $C_{3-4}$-alkynyl include 1-propynyl, 2-propynyl, 1-butynyl, 2-butynyl, and 1-methylprop-2-yn-1-yl.

Unless otherwise stated or indicated, the term "$C_{3-7}$-cycloalkyl" denotes a cyclic alkyl group having a ring size from 3 to 7 carbon atoms. Said cycloalkyl include cyclopropyl, cyclobutyl, cyclopentyl, cyclohexyl, and cycloheptyl. For parts of the range "$C_{3-7}$-cycloalkyl" all subgroups thereof are contemplated such as $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-6}$-cycloalkyl, $C_{5-7}$-cycloalkyl, $C_{6-7}$-cycloalkyl, etc.

Unless otherwise stated or indicated, the term "$C_{3-4}$-cycloalkyl-$C_{1-3}$-alkyl" denotes a straight or branched $C_{1-3}$-alkyl group substituted by a $C_{3-4}$-cycloalkyl group. An exemplary "$C_{3-4}$-cycloalkyl-$C_{1-3}$-alkyl" group includes cyclopropylmethyl.

Unless otherwise stated or indicated, the term "hydroxy-$C_{3-7}$-cycloalkyl" denotes a cyclic alkyl group having a ring size from 3 to 7 carbon atoms, that has a hydrogen atom thereof replaced with OH. Examples of said hydroxy-$C_{3-7}$-cycloalkyl include 1-hydroxy-cyclopropyl, 2-hydroxy-cyclopropyl, 1-hydroxy-cyclobutyl, 2-hydroxy-cyclobutyl, etc.

Unless otherwise stated or indicated, the term "$C_{3-4}$-cycloalkyl(hydroxy)-$C_{1-3}$-alkyl" denotes a straight or branched $C_{1-3}$-alkyl group substituted by a $C_{3-4}$-cycloalkyl group and a hydroxy group. Said $C_{3-4}$-cycloalkyl and hydroxy groups may be attached to the same or to different carbon atoms of the $C_{1-3}$-alkyl group. Preferably, the $C_{3-4}$-cycloalkyl and hydroxy groups are attached to the same carbon atom. An exemplary "$C_{3-4}$-cycloalkyl(hydroxy)-$C_{1-3}$-alkyl" group includes cyclopropyl(hydroxy)-methyl.

Unless otherwise stated or indicated, the term "methyl-$C_{3-7}$-cycloalkyl" denotes a $C_{3-7}$-cycloalkyl group substituted by one or two methyl groups. Examples of said "methyl-$C_{3-7}$-cycloalkyl" include 4-methylcyclohexyl, 3,3-dimethylcyclopentyl and 1-methylcyclopropyl.

Unless otherwise stated or indicated, the term "methyl-$C_{3-7}$-cycloalkoxy" denotes a $C_{3-7}$-cycloalkoxy group substituted by one or two methyl groups. Examples of said "methyl-$C_{3-7}$-cycloalkoxy" include 4-methylcyclohexyloxy, 3,3-dimethylcyclopentyloxy and 1-methylcyclopropyloxy.

Unless otherwise stated or indicated, the term "fluoro-$C_{3-7}$-cycloalkyl" denotes a $C_{3-7}$-cycloalkyl group substituted by one or two fluorine atoms. Examples of said "fluoro-$C_{3-7}$-cycloalkyl" include 2,2-difluorocyclopropyl and 4-fluorocyclohexyl.

Unless otherwise stated or indicated, the term "fluoro-$C_{3-7}$-cycloalkoxy" denotes a $C_{3-7}$-cycloalkoxy group substituted by one or two fluorine atoms. Examples of said "fluoro-$C_{3-7}$-cycloalkoxy" include 2,2-difluorocyclopropyloxy and 4-fluorocyclohexyloxy.

Unless otherwise stated or indicated, the term "aryl" refers to a hydrocarbon ring system of one, two, or three, preferably one or two, rings, having at least one aromatic ring and having from 6-14, preferably 6-10, carbon atoms. Examples of aryls are phenyl, pentalenyl, indenyl, indanyl, 1,2,3,4-tetrahydronaphthyl, 1-naphthyl, 2-naphthyl, fluorenyl and anthryl. The aryl rings may be optionally substituted. Likewise, aryloxy refers to an aryl group bonded to an oxygen atom.

An aryl group can be linked to the remainder of the molecule through any available ring carbon whether the ring carbon is in an aromatic ring or in a partially saturated ring.

The term "heteroaryl" refers to a mono- or bicyclic aromatic ring system, only one ring need be aromatic, and the said heteroaryl moiety can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings include furyl, pyrrolyl, thienyl, oxazolyl, isoxazolyl, imidazolyl, thiazolyl, isothiazolyl, imidazothiazolyl, pyridinyl, pyrimidinyl, pyrazinyl, chromanyl, quinazolinyl, indolyl, isoindolyl, indolinyl, isoindolinyl, indazolyl, pyrazolyl, pyridazinyl, quinolinyl, isoquinolinyl, benzofuranyl, dihydrobenzofuranyl, benzodioxolyl, benzodioxinyl, benzothienyl, benzimidazolyl, benzothiazolyl, benzothiadiazolyl, and benzotriazolyl groups. If a bicyclic heteroaryl ring is substituted, it may be substituted in any ring.

Unless otherwise stated or indicated, the term "heterocyclic" refers to a non-aromatic (i.e., partially or fully saturated) mono- or bicyclic ring system having 4 to 10 ring atoms with at least one heteroatom such as O, N, or S, and the remaining ring atoms are carbon. Preferably, "heterocyclic" refers to a fully saturated non-aromatic monocyclic ring system with 4 to 7 ring atoms and in which one or two atoms are heteroatoms selected from O, N and S, and the remaining ring atoms are carbon. Examples of heterocyclic groups include piperidyl, tetrahydropyranyl, tetrahydrofuranyl, azepinyl, azetidinyl, pyrrolidinyl, morpholinyl, imidazolinyl, thiomorpholinyl, pyranyl, dioxanyl, and piperazinyl groups. When present in heterocyclic groups, the sulfur atom may optionally be in an oxidized form (i.e., S=O or O=S=O).

Unless otherwise stated or indicated, the term "carbocyclic" refers to a non-aromatic (i.e., partially or fully saturated) monocyclic ring system having 3 to 6 carbon ring atoms. Examples of carbocyclic rings include cyclopropane, cyclobutane, cyclopentane, cyclohexane, cyclopentene, cyclohexene.

Unless otherwise stated or indicated, the term "halogen" shall mean fluorine, chlorine, bromine or iodine.

The term —S(O)$_e$R$^7$, wherein e is 0, 1, 2 or 3, has the meaning as illustrated by formula (VI)-(IX):

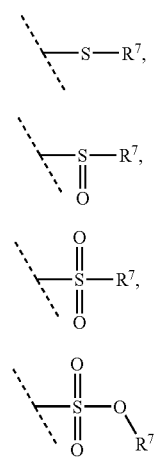

The term "lactam" refers to a lactam group selected from 2-azetidinon-1-yl, 2-pyrrolidon-1-yl and 2-piperidinon-1-yl.

The term "sultam" refers to a sultam group selected from tetrahydro-1,1-dioxido-2H-1,2-thiazin-2-yl and 1,1-dioxido-2-isothiazolidinyl.

Unless otherwise stated or indicated, the term "oxo" denotes =O (i.e., an oxygen atom joined to a carbon atom through a double bond).

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8$^{th}$ ed., Mc-Graw-Hill, Int. Ed. 1992, "Biotransformation of Drugs", p. 13-15; and "The Organic Chemistry of Drug Design and Drug Action" by Richard B. Silverman. Chapter 8, p 352. (Academic Press, Inc. 1992. ISBN 0-12-643730-0).

The following abbreviations have been used:
eq. means equivalents
CV means Coefficient of Variation,
DCM means dichloromethane,
DMSO means dimethyl sulphoxide,
EDTA means ethylenediamine tetraacetic acid,
EGTA means ethylenebis(oxyethylenenitrilo)tetraacetic acid,
HEPES means 4-(2-hydroxyethyl)-1-piperazineethanesulfonic acid,
HPLC means high performance liquid chromatography,
LSD means lysergic acid, diethylamide,
MeCN means acetonitrile,
SPA means Scintillation Proximity Assay,
TFA means trifluoroacetic acid,
THF means tetrahydrofuran,
UV means ultraviolet,
MeOH means methanol,
MW means microwave oven,
Boc means t-butoxycarbonyl,
LAH means lithium aluminum hydride,
TEA means triethylamine.

All isomeric forms possible (pure enantiomers, diastereomers, tautomers, racemic mixtures and unequal mixtures of two enantiomers) for the compounds delineated are within the scope of the invention. Such compounds can also occur as cis- or trans-, E- or Z-double bond isomer forms. All isomeric forms are contemplated.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parentral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

In a further aspect the invention relates to methods of making compounds of any of the formulae herein comprising reacting any one or more of the compounds of the formulae delineated herein, including any processes delineated herein. The compounds of the formula (I) above may be prepared by, or in analogy with, conventional methods.

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds.

In addition, various synthetic steps may be performed in an alternate sequence or order to give the desired compounds. Synthetic chemistry transformations useful in synthesizing applicable compounds are known in the art and include, for example, those described in R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The necessary starting materials for preparing the compounds of formula (I) are either known or may be prepared in analogy with the preparation of known compounds. The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Methods

[1]H nuclear magnetic resonance (NMR) and $^{13}$C NMR were recorded on a Bruker Advance DPX 400 spectrometer at 400.1 and 100.6 MHz, respectively, or alternatively, on a Varian Inova 400 spectrometer at 400 and 100.5 MHz respectively, or alternatively, on a Bruker NMR 500 spectrometer at 500.1 MHz and 125.1 MHz, respectively or alternatively, on a JEOL eclipse 270 spectrometer at 270.0 MHz and 67.5 MHz, respectively. All spectra were recorded using residual solvent as internal standard.

Preparative HPLC/MS was performed on a Waters/Micromass Platform ZQ system and preparative HPLC/MS was performed on a Gilson system in accordance to the experimental details specified in the examples. Analytical HPLC-MS was performed using an Agilent 1100 Series Liquid Chromatograph/Mass Selective Detector (MSD) to obtain the pseudo molecular [M+H]$^+$ ion of the target molecules. Preparative flash chromatography was performed on Merck silica gel 60 (230-400 mesh). The compounds were named using ACD Name 6.0 (or later versions thereof). Microwave reactions were performed with a Personal Chemistry Smith Creator using 0.5-2 mL or 2-5 mL Smith Process Vials fitted with aluminum caps and septa.

INTERMEDIATE 1

3,4-Dihydropyrrolo[4,3,2-de]isoquinolin-5(1H)-one

This intermediate was prepared according to a literature procedure (M. E. Flaugh, T. A. Crowell, J. A. Clemens, B. D. Sawyer *J. Med. Chem.* 1979, 22, 63-68).

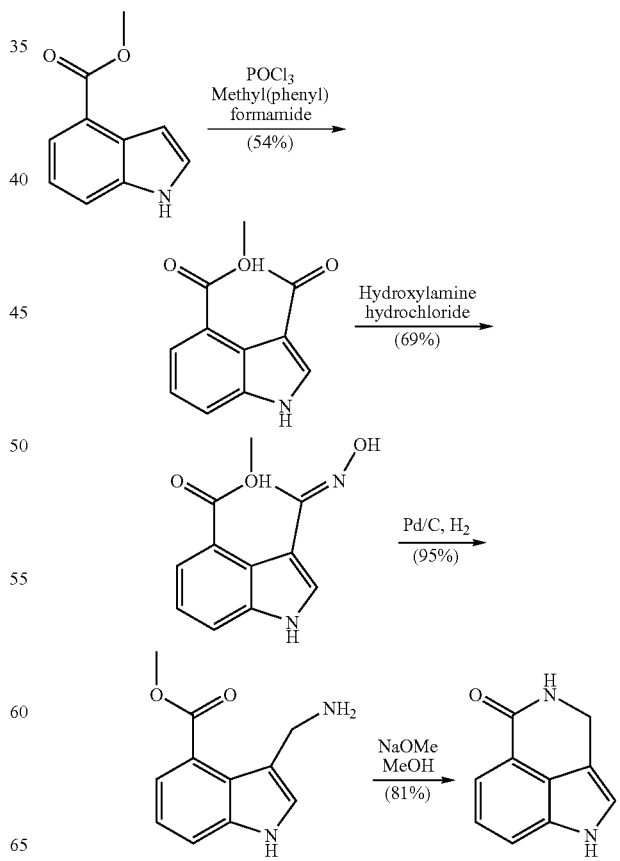

INTERMEDIATE 2

1-(Phenylsulfonyl)-3,4-dihydropyrrolo[4,3,2-de]isoquinolin-5(1H)-one

Benzenesulfonyl chloride (140 mg, 0.79 mmol), NBu$_4$HSO$_4$ (24 mg, 0.07 mmol) and 4M aq. NaOH (2 mL) were, in that order, added to 3,4-Dihydropyrrolo[4,3,2-de]isoquinolin-5(1H)-one, Intermediate 1 (124 mg, 0.72 mmol) in DCM (10 mL). The reaction was stirred at room temperature for 2 h and then extracted with water and DCM (×2). The product seems to be only partially soluble in DCM and some solid material in the water layer was filtered off and added to the DCM layer, which was concentrated and dried to give 227 mg of the title compound, as a light brown solid. MS m/z 313 [M+H]$^+$.

EXAMPLE 1

1-(Phenylsulfonyl)-1,3,4,5-tetrahydropyrrolo[4,3,2-de]isoquinoline

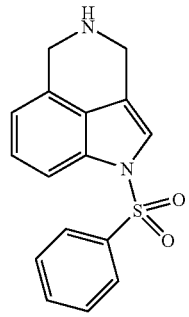

BH$_3$:SMe$_2$ (205 µL, 2.2 mmol) was added dropwise over 5 min. to a refluxing mixture of 1-(phenylsulfonyl)-3,4-dihydropyrrolo[4,3,2-de]isoquinolin-5(1H)-one, Intermediate 2, (225 mg, 0.72 mmol) in dry THF (10 mL) with continuous reflux for 2.5 h. Additional two portions BH$_3$:SMe$_2$ (100 µL×2) were added (2.5 h reflux between the additions). Reflux was continued for 5 h after the last addition, then room temperature over night. The reaction was quenched by addition of HCl in MeOH (1.25 M, 4 mL) and reflux 1 h. The solvent was evaporated and the crude mixture was extracted with DCM (×2) and sat. Na$_2$CO$_3$(aq). The organic layers were combined, dried and concentrated. Purification was performed by flash column chromatography (3-5% MeOH in DCM) which gave 66 mg of the title compound as a beige solid. MS m/z 299 [M+H]$^+$.

EXAMPLE 2

4-Methyl-1-(phenylsulfonyl)-1,3,4,5-tetrahydropyrrolo[4,3,2-de]isoquinoline trifluoroacetate

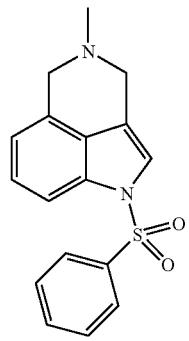

Formaldehyde (37% in water, 55 µL, 0.76 mmol) and NaBH$_3$CN (104 mg, 1.65 mmol) were added to 1-(phenylsulfonyl)-1,3,4,5-tetrahydropyrrolo[4,3,2-de]isoquinoline, Example 1 (23 mg, 0.07 mmol) in dry MeCN (3 mL). The reaction was irradiated with microwaves for 10 min. at 130° C., filtered and concentrated. The crude product was purified by preparative HPLC (YMC column 150×30 mm, 20-50% MeCN, 0.1% TFA). This gavel 7 mg of the title compound as a brown gum. MS m/z 313 [M+H]$^+$.

EXAMPLE 3

4-(1H-Imidazol-2-ylmethyl)-1-(phenylsulfonyl)-1,3,4,5-tetrahydropyrrolo[4,3,2-de]isoquinoline bis(trifluoroacetate)

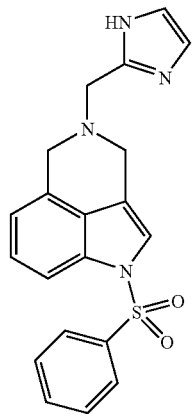

The experimental for Example 2 was followed using 1H-imidazole-2-carbaldehyde (16 mg, 0.18 mmol), AcOH (46 µL, 0.81 mmol), Na(OAc)$_3$BH$_3$ (51 mg, 0.24 mmol) and 1-(phenylsulfonyl)-1,3,4,5-tetrahydropyrrolo[4,3,2-de]isoquinoline, Example 1 (27 mg, 0.08 mmol) in dry THF (4 mL). Preparative HPLC (YMC column 150×30 mm, 32-62% MeCN, 0.1% TFA). This gave 1.7 mg of the title compound, as a brown gum. MS m/z 379 [M+H]$^+$.

INTERMEDIATE 3

1,3,4,5-tetrahydropyrrolo[4,3,2-de]isoquinoline

LAH (1M in THF, 8.7 mL, 8.7 mmol) was added to 3,4-Dihydropyrrolo[4,3,2-de]isoquinolin-5(1H)-one, Intermediate 1 (300 mg, 1.72 mmol) in dry THF (only partly dissolved) under N$_2$. The mixture was stirred at reflux for 2 h and a color change from light brown to green was noticed after 1 h. Water (330 µL), NaOH (aq., 15%, 330 µL) and water (1.0 mL) were, in that order, added and the resulting precipitation was filtered off. The eluate was dried (Na$_2$SO$_4$), filtered and concentrated to give the crude product. The material was used without further purification.

EXAMPLE 4

N,N-Dimethyl-2-[1-(phenylsulfonyl)-1,5-dihydropyrrolo[4,3,2-de]isoquinolin-4(3H)-yl]ethanamine bis(trifluoroacetate)

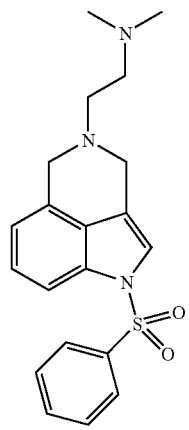

1,3,4,5-tetrahydropyrrolo[4,3,2-de]isoquinoline, Intermediate 3 (45 mg, 0.28 mmol), NEt$_3$ (236 µL, 1.71 mmol) and N,N-dimethylglycyl chloride hydrochloride (90 mg, 0.57 mmol) were dissolved in dry DCM (10 mL) by sonication and stirred at room temperature for 1.5 h. The mixture was extracted with DCM (×2) and aq. sat. Na$_2$CO$_3$/brine. The organic layers were combined dried (Na$_2$SO$_4$), filtered and concentrated to give 69 mg crude material. ⅖ of this material (28 mg, 0.12 mmol) was added to dry THF (3 mL, not dissolved) and LAH (1M in THF, 0.575 mL, 0.575 mmol) was added. The mixture was stirred at reflux for 60 min. (clear solution). Water (22 µL), 15% aq. NaOH (22 µL) and water (66 µL) were added and the resulting precipitation was filtered off. The eluate was dried (Na$_2$SO$_4$), filtered and concentrated to give 26 mg crude material. Half of this material (13 mg, 0.057 mmol) was dissolved in dry THF (2 mL) and NaH (60% dispersion in mineral oil, 11 mg, 0.28 mmol)) was added. The mixture was stirred at ambient temperature for 50 min., then phenylsulfonyl chloride (8 mL, 0.06 mmol) in dry THF (0.5 mL) was added with continuous stirring for 1 h. The reaction was cooled on ice bath and quenched with 2 drops of water, acidified with 1 drop of conc. HCl and concentrated. The crude product was purified by preparative HPLC (ACE-column 50×21.1 mm, 16-46% MeCN, 0.1% TFA). This gave 15 mg of the title compound as a colorless solid. MS m/z 370 [M+H]$^+$.

EXAMPLE 5

4-Ethyl-1-(phenylsulfonyl)-1,3,4,5-tetrahydropyrrolo[4,3,2-de] isoquinoline trifluoroacetate

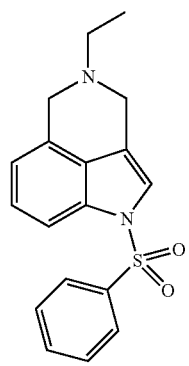

Acetaldehyde (11 µL, 0.18 mmol), AcOH (34 µL, 0.60 mmol) and Na(OAc)$_3$BH$_3$ (52 mg, 0.24 mmol) were added to 1-(phenylsulfonyl)-1,3,4,5-tetrahydropyrrolo[4,3,2-de]isoquinoline, Example 1 (18 mg, 0.06 mmol) in dry THF (3 mL). The reaction mixture was irradiated with microwaves for 12 min. at 130° C., filtered and concentrated. The crude product was purified by preparative HPLC (ACEcolumn 50×21.1 mm, 15-45% MeCN, 0.1% TFA). This gave 8 mg of the title compound as a colorless gum. MS m/z 327 [M+H]$^+$.

EXAMPLE 6

1-(phenylsulfonyl)-4-(pyrrolidin-2-ylmethyl)-1,3,4,5-tetrahydropyrrolo[4,3,2-de]isoquinoline bis(trifluoroacetate)

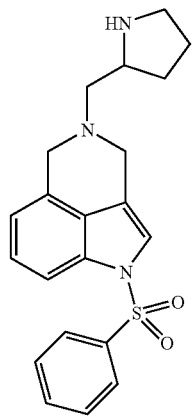

Tert-butyl 2-formylpyrrolidine-1-carboxylate (18 mg, 0.09 mmol), AcOH (17 µL, 0.30 mmol) and Na(OAc)$_3$BH$_3$ (26 mg, 0.12 mmol) were added to 1-(phenylsulfonyl)-1,3,4,5-tetrahydropyrrolo[4,3,2-de]isoquinoline, Example 1 (9 mg, 0.03 mmol) in dry THF (3 mL). The reaction mixture was irradiated with microwaves for 12 min. at 130° C., filtered and concentrated. The residue was dissolved in MeOH/conc. HCl (4:1, 1.5 mL) and irradiated with microwaves for 3 min. at 100° C., filtered and concentrated. The crude product was purified by preparative HPLC (ACE column 50×21.1 mm, 11-41% MeCN, 0.1% TFA). This gave 11 mg of the title compound as a light yellow gum. MS m/z 382 [M+H]$^+$.

EXAMPLE 7

1-(Phenylsulfonyl)-4-(pyrrolidin-3-ylmethyl)-1,3,4,5-tetrahydropyrrolo[4,3,2-de]isoquinoline trifluoroacetate

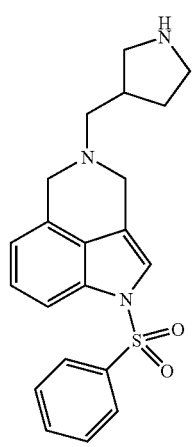

The experimental for Example 6 was followed using tert-butyl 3-formylpyrrolidine-1-carboxylate (18 mg, 0.09 mmol). Preparative HPLC (ACE column 50×21.1 mm, 9-39% MeCN, 0.1% TFA). This gave 11 mg of the title compound as a colorless gum. MS m/z 382 [M+H]⁺.

INTERMEDIATE 4

4-Ethyl-1,3,4,5-tetrahydropyrrolo[4,3,2-de]isoquinoline

LiAlH₄ (0.440 g, 11.6 mmol) was added in portions to a solution of 3,4-dihydropyrrolo[4,3,2-de]isoquinolin-5(1H)-one, Intermediate 1 (0.4 g, 2.32 mmol) in dry THF (20 ml). The mixture was brought to reflux for 3 hours, cooled, diluted with aqueous THF and filtered. The solid cake was washed with THF (2×) and the residue was evaporated to give a light brown solid. This brown solid was dissolved in MeOH (20 ml) and acetaldehyde (0.334 g, 7.6 mmol) and sodium triacetoxy borohydride (0.482 g, 2.3 mmol) were added. The mixture was stirred for 1 hour and evaporated to half its volume and partitioned between 1N Na₂CO₃ and dichloromethane. The organic phase was washed with brine, dried (MgSO₄) and evaporated. The crude product was purified by flash chromatography using 10% MeOH to 50% MeOH in dichloromethane with 1% NEt₃. Yield: 142 mg. Grey solid. MS m/z 187 [M+H]⁺.

General Procedure for Sulfonylation Used in Example 8-11:

4-Ethyl-1,3,4,5-tetrahydropyrrolo[4,3,2-de]isoquinoline, Intermediate 4 (0.015 g, 0.081 mmol), requisite sulfonyl chloride (0.16 mmol) and tetrabutylammonium hydrogensulfate (5 mg, 0.016 mmol) were dissolved in dichloromethane (1 ml) and NaOH (0.01 g, 0.24 mmol) in water (0.3 ml) was added. The mixture was stirred at room temperature overnight and water (1 ml) was added to each vial and the organic phase was collected, evaporated and purified as described below.

EXAMPLE 8

1-[(2-Chlorophenyl)sulfonyl]-4-ethyl-1,3,4,5-tetrahydropyrrolo[4,3,2-de] isoquinoline

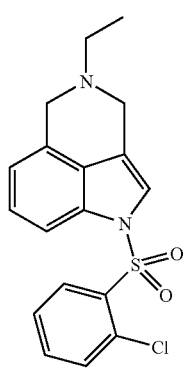

Sulfonyl chloride: 2-chlorophenylsulfonyl chloride (34 mg, 0.16 mmol). Purified by reversed phase preparative HPLC using XTerra Prep MS C18 5 μm 19×50 mm, flow 25 ml/min, 50 mM pH10 NH₄HCO₃/ACN, fractions collected based on UV-signal (254 nm). Prep Gradient start 37. Prep gradient stop 67. The purest fractions were pooled and the acetonitrile was evaporated. Yield: 8.6 mg. Light yellow solid. MS m/z 361 [M+H]⁺.

EXAMPLE 9

4-Ethyl-1-{[2-(trifluoromethyl)phenyl]sulfonyl}-1,3,4,5-tetrahydropyrrolo[4,3,2-de]isoquinoline

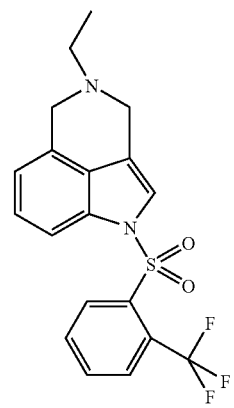

Sulfonyl chloride: 2-(trifluoromethyl)benzenesulfonyl chloride (39 mg, 0.16 mmol). Purified by reversed phase preparative HPLC using XTerra Prep MS C18 5 μm 19×50 mm, flow 25 ml/min, 50 mM pH10 NH₄HCO₃/ACN, fractions collected based on UV-signal (254 nm). Prep Gradient start 39. Prep gradient stop 69. The purest fractions were pooled and evaporated. Yield: 6.7 mg. Brown solid. MS m/z 395 [M+H]⁺.

EXAMPLE 10

1-(1-Benzothien-2-ylsulfonyl)-4-ethyl-1,3,4,5-tetrahydropyrrolo[4,3,2-de]isoquinoline

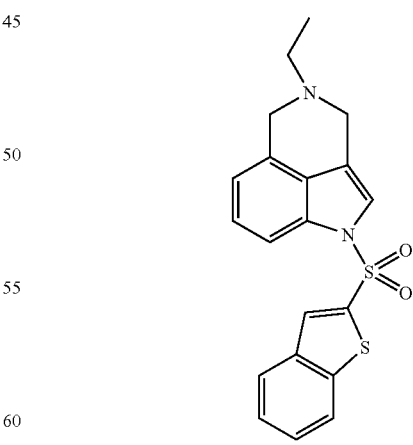

Sulfonylchloride: 1-benzothiophene-2-sulfonyl chloride (38 mg, 0.16 mmol). Purified by reversed phase preparative HPLC using XTerra Prep MS C18 5μm 19×50 mm, flow 25 ml/min, 50 mM pH10 NH₄HCO₃/ACN, fractions collected based on UV-signal (254 nm). Prep Gradient start 44. Prep gradient stop 74. The purest fractions were pooled and evaporated. Yield: 1.1 mg. Yellow solid. MS m/z 383 [M+H]$^+$.

EXAMPLE 11

4-Ethyl-1-[(2-methoxy-5-methylphenyl)sulfonyl]-1,3,4,5-tetrahydropyrrolo[4,3,2-de]isoquinoline

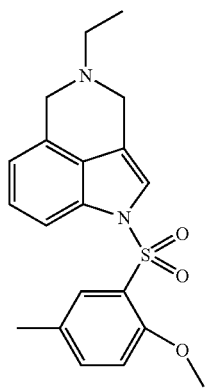

Sulfonyl chloride: 6-methoxy-m-toluenesulfonylchloride (0.035 g, 0.16 mmol). Purified by reversed phase preparative HPLC using XTerra Prep MS C18 5 µm 19×50 mm, flow 25 ml/min, 50 mM pH10 NH$_4$HCO$_3$/ACN, fractions collected based on UV-signal (254 nm). Prep Gradient start 36. Prep gradient stop 66. The purest fractions were pooled and evaporated. Yield: 0.5 mg. Off white solid. MS m/z 371 [M+H]$^+$.

INTERMEDIATE 5

1-(Phenylsulfonyl)-1H-indole-4-carbaldehyde

1H-Indole-4-carbaldehyde (24.8 g, 0.17 mol) was dissolved in dry DMF (500 ml), cooled in ice-bath and NaH (7.5 g (60% suspension in oil), 0.19 mol, 1.1 eq.) was added. After stirring for a few minutes, the cold bath was removed and the rxn mixture was stirred at room temperature for 40 min. under Ar. The insoluble NaH clumps were brought in solution by means of sonication for a few minutes. The mixture was cooled in ice-bath and benzenesulfonyl chloride (23.9 ml, 0.188 mol, 1.1 e.q.) was added dropwise over 3 min. The reaction mixture was stirred at room temperature for 1 hour, then poured slowly into a mixture of water (1 L) and EtOAc (200 ml). The aqueous phase was extracted with EtOAc (5×100 ml), the organic phase was washed with brine (200 ml), dried over Na$_2$SO$_4$ and evaporated. The residue was purified on silica flash column using petroleum ether/EtOAc (1:1) giving the product as a colorless crystalline solid. Yield: 45.5 g. MS m/z 286 [M+H]$^+$.

INTERMEDIATE 6

4-[(E)-2-Nitrovinyl]-1-(phenylsulfonyl)-1H-indole 1-(Phenylsulfonyl)-1H-indole-4-carbaldehyde, Intermediate 5 (45.4 g, 0.159 mol) was dissolved in nitromethane (300 ml) and ammonium acetate (4.9 g, 0.064 mol, 0.4 eq.) was added. Mixture was heated at reflux for 4 hours and left overnight at ROOM TEMPERATURE Water (150 ml) was added, organic phase was separated. The aqueous phase was extracted with DCM (3×50 ml). Combined organic phase was washed with brine and dried on Na$_2$SO$_4$. The crude material (HPLC purity 85%) was passed through a silica column using DCM/EtOAc (8:1) as eluent. The product containing fractions were evaporated to a small volume when crystallization started. The yellow crystals were filtered, washed with petro/ether/EtOAc (2:1), and dried in vacuo. Yield: 33.1 g. MS m/z 329 [M+H]$^+$.

INTERMEDIATE 7

2-[1-(Phenylsulfonyl)-1H-indol-4-yl]ethanamine

4-[(E)-2-nitrovinyl]-1-(phenylsulfonyl)-1H-indole, Intermediate 6 (32.1 g, 97.8 mmol) was mixed with dry THF (100 ml), stirred for 5 min, then dry MeOH was added (400 ml). Mixture was cooled in ice-bath and sodium borohydride (14.8 g, 0.39 mol) was added in small portions over a period of 30 minutes.

Preparation of NiB$_2$ catalyst: Nickel (II) chloride hexahydrate (46.5 g, 0.196 mol) was dissolved in MeOH (200 ml), the solution cooled in ice-bath and sodium borohydride (22.3 g, 0.587 mol) was added in small portions with vigorous stirring over 30 min. (N.B. Reaction is very exothermic with vigorous gas evolution!) The black suspension is stirred for additional 15 minutes at ROOM TEMPERATURE This catalyst suspension is added to the main reaction mixture at 0° C. and sodium borohydride (38 g, 1.0 mol) is carefully added in small portions over 1 hour. Reaction mixture was stirred for additional 2 hours at room temperature, filtered through a pad of MeOH/NH$_3$ aq. impregnated silica. The silica pad was washed with MeOH/NH$_3$ aq. and MeOH was evaporated in vacuo from the filtrate. Water (500 ml) was added to the residue and the mixture was extracted with diethylether. The organic layer was washed with brine, dried over Na$_2$SO$_4$, evaporated and the residue was purified on silica using DCM/MeOH/NH$_3$ aq. (40:8:0.5), giving the desired amine as a syrup. Yield: 12.2 g. MS m/z 301 [M+H]$^+$.

EXAMPLE 12

1-(Phenylsulfonyl)-3,4,5,6-tetrahydro-1H-azepino[3,4,5-cd]indole hydrochloride

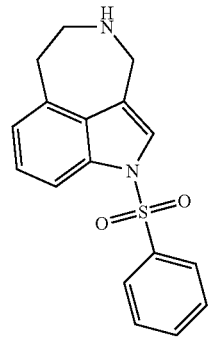

2-[1-(Phenylsulfonyl)-1H-indol-4-yl]ethanamine, Intermediate 7 (7.05 g, 23.5 mmol) was dissolved in formic acid (70 ml) and formaldehyde solution (14 ml, as a 37% sol. in water, 187 mmol) was added. Reaction mixture was stirred at room temperature for 20 hours, poured into water (700 ml) and extracted with DCM. The DCM extract was washed with 2% NaOH solution in water (500 ml), brine, dried on Na$_2$SO$_4$ and evaporated. The residue was purified on silica using DCM/MeOH/NH$_3$ aq. (50:5:0.5), giving the desired amine as a syrup. This material was dissolved in EtOAc and saturated HCl solution in dioxane was added dropwise until precipitation was complete. Solution was diluted with diethylether, the salt was filtered off, washed with diethylether and dried. The dry salt was dissolved in i-PrOH/MeOH by heating, MeOH was removed on rotavap and diethylether was added slowly giving crystalline off-white precipitate of the desired product, which was filtered, washed with ether and dried in vacuo. Yield: 4.2 g. MS m/z 313 [M+H]$^+$.

EXAMPLE 13

4-Methyl-1-(phenylsulfonyl)-3,4,5,6-tetrahydro-1H-azepino[3,4,5-cd]indole hydrochloride

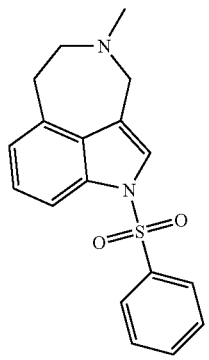

1-(Phenylsulfonyl)-3,4,5,6-tetrahydro-1H-azepino[3,4,5-cd]indole hydrochloride, Example 12 (100 mg, 0.3 mmol) was dissolved in THF (4 mL) before sodium triacetoxyborohydride (203 mg, 1.0 mmol) and acetic acid (191 mg, 3.2 mmol) was added. Aqueous formaline (37%, 1 mL) was added and the reaction mixture was heated in MW at 70° C. for 300 s. The reaction mixture was evaporated and the crude product was purified by preparative HPLC using System B, 100 mM NH$_4$HCO$_3$/MeCN (36-66% MeCN). The product was isolated and transformed to the hydrochloride. 15.2 mg of the pure product was isolated as an yellow oil, yield 12%. MS m/z 327 [M+H]$^+$.

EXAMPLE 14

4-Ethyl-1-(phenylsulfonyl)-3,4,5,6-tetrahydro-1H-azepino[3,4,5-cd]indole hydrochloride

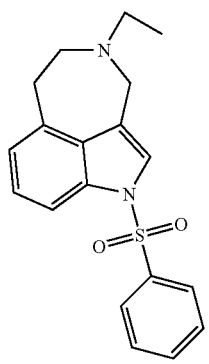

1-(Phenylsulfonyl)-3,4,5,6-tetrahydro-1H-azepino[3,4,5-cd]indole hydrochloride, Example 12 (70 mg, 0.2 mmol) was dissolved in THF (4 mL) before sodium triacetoxyborohydride (142 mg, 0.7 mmol) and acetic acid (134 mg, 2.2 mmol) was added. acetaldehyde (14.7 mg, 0.3 mmol) was added and the reaction mixture was heated in MW at 70° C. for 600 s. The reaction mixture was evaporated and the crude product was purified by preparative HPLC (33-63), using Xterra column. The product was isolated and transformed to the hydrochloride. 12.9 mg of the pure product was isolated as a clear oil. MS m/z 341 [M+H]$^+$.

INTERMEDIATE 8

2-Nitroethyl Acetate

This compound was prepared according to M. E. Flaugh, T. A. Crowell, J. A. Clemens, B. D. Sawyer *J. Med. Chem.*, 1979, 22, pp. 63-68. Acetic anhydride (8.06 g, 79.0 mmol) and NaOAc (1.45 g, 17.7 mmol) were mixed and heated. Two drops of pyridine were added. 2-nitroethanol (6.45 g, 70.8 mmol) was carefully added to the suspension at 30-35° C. during 30 min. Thereafter the mixture was stirred overnight at room temperature. The next morning the mixture contained undissolved NaOAc and a new orange precipitate. The reaction mixture was taken up between CHCl$_3$ and water, washed 1× with water, 1× with brine and dried with MgSO$_4$. Thereafter the solvent was evaporated under reduced pressure at 40° C. The remaining orange oil was co-evaporated first with chloroform and then five times with toluene and finally with chloroform to get the 6.90 g of pure compound.

INTERMEDIATE 9

Methyl 3-(2-Nitroethyl)-1H-indole-4-carboxylate

A solution of methyl 1H-indole-4-carboxylate (7.34 g, 41.9 mmol), 2-nitroethyl acetate (6.90 g, 51.9 mmol) and 4-tert-butylcatechol (0.026 g, 0.16 mmol) in xylene (50 mL) was refluxed for 6 hrs. The solvent was evaporated under reduced pressure to give a residual dark oily raw product that was purified by short column chromatography on silica using ethyl acetate-light petroleum as eluent. The product was obtained as yellowish solid material in 79% yield. Mp: 103° C. MS m/z 249 [M+H]$^+$.

INTERMEDIATE 10

1,3,4,5-Tetrahydro-6H-azepino[5,4,3-cd]indol-6-one

Methyl 3-(2-nitroethyl)-1H-indole-4-carboxylate, Intermediate 9 (7.38 g, 29.8 mmol) was dissolved in methanol (200 mL) by heating and aqueous 2M HCl (460 mL) was added. Zinc powder (46.2 g, 706 mmol) was added portion vise by vigorous stirring. The resulting mixture was heated under reflux for 2 h. The hot reaction mixture was filtered and the filtrate was treated with aqueous 2M NaOH (560 mL) and filtered again. The filter cake was washed with methanol. The methanol was removed under reduced pressure and the aqueous mixture was extracted three times with ethyl acetate. The organic solution was washed with water and brine dried with magnesium sulfate, filtered and evaporated to dryness. It was obtained a yellowish crystalline material with the yield of 4.62 g. Recrystallisation from the dichlomethane-methanol mixture gave the product of very high purity. Mp. 234° C. MS m/z 187 [M+H]$^+$.

INTERMEDIATE 11

1,3,4,5-Tetrahydro-6H-azepino[5,4,3-cd]indol and 2,2a,3,4,5,6-hexahydro-1H-azepino[5,4,3-cd]indole Intermediate 10 (175 mg, 0.94 mmol) was added to phosphoryl chloride (1 mL) at room temperature. The solution was stirred for 15 min and excess phosphoryl chloride then removed at room temperature under vacuum. The resultant oil was placed under high vacuum for 20 min to remove residual phosphoryl chloride and then dissolved in glyme (4 mL). The solution was cooled in ice and sodium borohydride (114 mg, 3 mmol) was added with vigorous stirring. The reaction mixture was warmed to room temperature, stirred for 1 h, and cooled in ice and 10% hydrochloric acid (2 mL) was added dropwise. The glyme was evaporated and water added. After extraction with ether, sodium hydroxide was added to the aqueous solution (to about pH 10), followed by extraction with ether. The basic extracts were dried over $MgSO_4$ and concentrated. The crude product were purified with column chromatography ($SiO_2$; $CHCl_3$: MeOH: $NH_3$ 95:4.5:0.5) and used directly in the next step. 30% of the starting material was recovered in this separation.

INTERMEDIATE 12 tert-butyl 1,3,4,6-tetrahydro-5H-azepino[5,4,3-cd]indole-5-carboxylate

The pure 1:1 mixture of 1,3,4,5-Tetrahydro-6H-azepino[5,4,3-cd]indole and 2,2a,3,4,5,6-hexahydro-1H-azepino[5,4,3-cd]indole, Intermediate 11 (172 mg, 1 mmol) was dissolved in DCM (10 mL) and added di-tert-butyl dicarbonate (436 mg, 2 mmol). The reaction mixture was stirred at room temperature over night. Solvent was removed and the residue was purified by chromatography ($SiO_2$, ethyl acetate:cyclohexane 1:5). The expected product tert-butyl 1,3,4,6-tetrahydro-5H-azepino[5,4,3-cd]indole-5-carboxylate was isolated from crude mixture of products and was pure enough for the next step synthesis.

EXAMPLE 15

1-(Phenylsulfonyl)-3,4,5,6-tetrahydro-1H-azepino[5,4,3-cd]indole

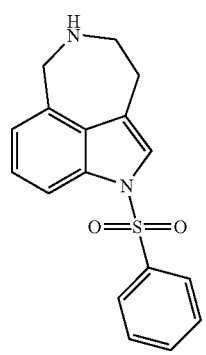

NaH (60% in mineral oil, 66 mg, 0.4 mmol) was added to a solution of tert-butyl 1,3,4,6-tetrahydro-5H-azepino[5,4,3-cd]indole-5-carboxylate, Intermediate 12 (51 mg, 0.2 mmol) in 800 of dry DMF). The reaction mixture was shaken at room temperature for 10 minutes and phenylsulfonyl chloride (66.2 mg, 0.4 mmol, in 600 uL of dry DMF) was added. The reaction mixture was shaken at room temperature for 10-20 minutes. The reaction was quenched by adding 4 mL of mixture a mixture of methanol and acetic acid (1:1). Boc-deprotection was carried out by adding 4 mL of solution of TFA/DCM (1:1). 2M $NH_3$ in MeOH was added to the crude reaction (2×10 mL) and the solvent was removed under vacuum. The crude product was purified by preparative HPLC using System B, 100 mM $NH_4HCO_3$/MeCN (10-50% MeCN). 50 mg of the pure product was isolated as an off-white solid. MS m/z 313 [M+H]$^+$.

EXAMPLE 16

5-Methyl-1-(phenylsulfonyl)-3,4,5,6-tetrahydro-1H-azepino[5,4,3-cd]indole

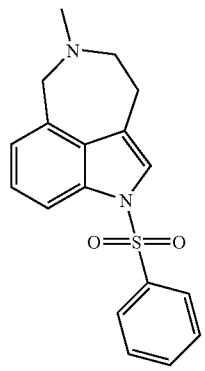

1-(Phenylsulfonyl)-3,4,5,6-tetrahydro-1H-azepino[5,4,3-cd]indol, Example 15 (34.4 mg, 0.11 mmol) was dissolved in DME (2 mL) and added formaldehyde (37% Wt. solution in water, 0.1 mL, 1.1 mmol), acetic acid (0.05 mL, 0.7 mmol) and sodium triacetoxyborohydride (156 mg, 0.7 mmol). The reaction mixture was stirred at room temperature for 24 H. The reaction was quenched by adding 1 M NaOH (5 mL). Aqueous phase (pH about 14) was separated and was then extracted with DCM (3×5 mL). The combined organic phases was washed with water and brine, and dried with MgSO4. The solvent was removed under vacuum. 20 mg pure product was obtained as an off-white solid. MS m/z 327 [M+H]$^+$.

INTERMEDIATE 13

6-Methyl-3,4,5,6-tetrahydro-1H-azepino[5,4,3-cd]indol-7-ol

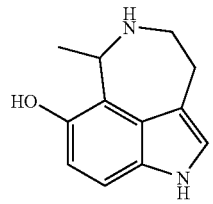

To a solution of serotonin*HCl (5.02 g, 23.6 mmol) in MeOH (200 mL) was added TEA (200 mL) and the mixture was stirred at room temperature for 30 min. The reaction mixture was then put under an oxygen atmosphere (balloon) and was stirred at reflux temperature (68° C.) for 24 hours. The solvent from the brown mixture was evaporated at reduced pressure and the resulting oil (10 g) was plug-applicated on a column of silica (L=90 mm q=60 mm) and chromatographed initially with CHCl$_3$/MeOH/(aq 25% NH3) 90/10/1 about two column volumes, followed by 80/20/2. The pure fractions were pooled and the solvent was evaporated at reduced pressure to give 0.41 g of a brown solid. MS m/z 203 [M+H]$^+$.

INTERMEDIATE 14 tert-Butyl 7-(acetyloxy)-6-methyl-1,3,4,6-tetrahydro-5H-azepino[5,4,3-cd]indole-5-carboxylate

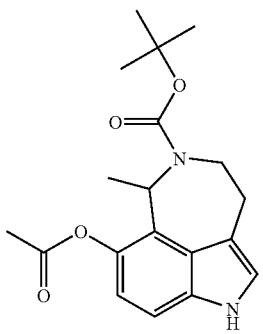

To a solution of 6-methyl-3,4,5,6-tetrahydro-1H-azepino[5,4,3-cd]indol-7-ol, Intermediate 13 (340 mg, 1.7 mmol) in MeOH (10 mL) was added (BOC)$_2$O (513 mg, 2.4 mmol) and the reaction mixture was stirred at room temperature for 30 minutes (95% conversion). Pyridine (0.5 mL) was added and the mixture was left at room temperature over night. The solvent was evaporated at reduced pressure and the resulting residue was dissolved in pyridine (4 mL), cooled on an ice bath, Ac$_2$O (1 mL) was added and the stirred mixture was allowed to slowly reach room temperature over night. The mixture was concentrated under reduced pressure and the residue was co-evaporated twice with toluene. The dark brown oil (0.9 g) was chromatographed on a column of silica, initially with 100% CHCl$_3$ followed by CHCl$_3$/MeOH 99.5/0.5. Evaporation of pure pooled fractions yielded 241 mg of the title compound as a light yellow oil. MS m/z 289 [M+H-isobutene]$^+$.

INTERMEDIATE 15 tert-Butyl 7-hydroxy-6-methyl-1-(phenylsulfonyl)-1,3,4,6-tetrahydro-5H-azepino[5,4,3-cd]indole-5-carboxylate

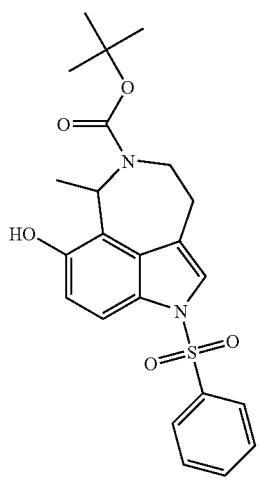

A solution of tert-butyl 7-(acetyloxy)-6-methyl-1,3,4,6-tetrahydro-5H-azepino[5,4,3-cd]indole-5-carboxylate, Intermediate 14 (241 mg, 0.7 mmol) in dry DMF (4 mL) was cooled on an ice bath, benzene sulphonyl chloride (210 mg, 1.2 mmol) was added and followed by NaH (34 mg, 1.4 mmol) added in small portions during one minute. The mixture was stirred for two minutes whereafter 2M NaOH (0.5 mL) was added and the mixture was left at room temperature over night. The mixture was diluted with water (10 mL) and HOAc (0.5 mL) was carefully added to the brown turbid solution resulting in the precipitation of an off white solid. More water (20 ml) was added and the solids were filtered off and dried to give 245 mg of off-white crystals. MS m/z 343 [M+H-Boc]$^+$.

EXAMPLE 17

7-Methoxy-6-methyl-1-(phenylsulfonyl)-3,4,5,6-tetrahydro-1H-azepino[5,4,3-cd]indole trifluoroacetate

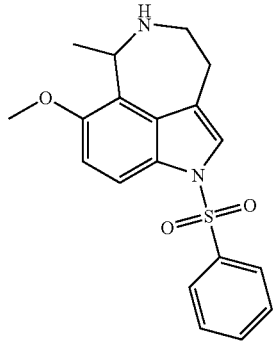

To a solution of tert-butyl 7-hydroxy-6-methyl-1-(phenylsulfonyl)-1,3,4,6-tetrahydro-5H-azepino[5,4,3-cd]indole-5-carboxylate, Intermediate 15, (39 mg, 0.079 mmol) in acetone (10 mL) was added K$_2$CO$_3$ (110 mg, 0.79 mmol) followed by MeI (79 mg, 0.55 mmol) and the mixture was heated at reflux over night. The solvent from the filtered solution was evaporated at reduced pressure and the resulting oil was dissolved in DCM/TFA 50/50 (1 mL) and was left at room temperature over night. The solvent was evaporated at reduced pressure, the resulting oil was dissolved in MeOH with a drop of 25% aq NH$_3$ and the crude was purified by preparative HPLC (Xterra C18, 10 mM NH$_4$CO$_3$ (pH 10)-CH$_3$CN) to give 11.9 mg of the title compound as a brown oil. MS m/z 357 [M+H]$^+$.

EXAMPLE 18

6-Methyl-1-(phenylsulfonyl)-3,4,5,6-tetrahydro-1H-azepino[5,4,3-cd]indol-7-ol

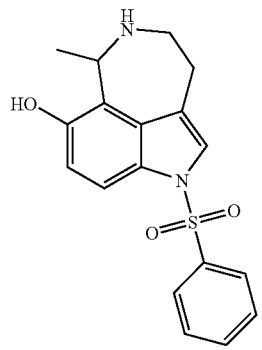

A 50/50 mixture of DCM/TFA (1 mL) was added to tert-butyl 7-hydroxy-6-methyl-1-(phenylsulfonyl)-1,3,4,6-tetrahydro-5H-azepino[5,4,3-cd]indole-5-carboxylate, Intermediate 15 (16 mg, 0.036 mmol) and the mixture was stirred at room temperature for one hour. The solvent was evaporated at reduced pressure and the crude product was purified by preparative HPLC (Xterra C18, 10 mM NH4CO3 (pH 10)-CH3CN) to give 6.9 mg of the title compound. MS m/z 343 [M+H]$^+$.

INTERMEDIATE 16 tert-Butyl 6-methyl-1-(phenylsulfonyl)-7-{[(trifluoromethyl)sulfonyl]oxy}-1,3,4,6-tetrahydro-5H-azepino[5,4,3-cd]indole-5-carboxylate

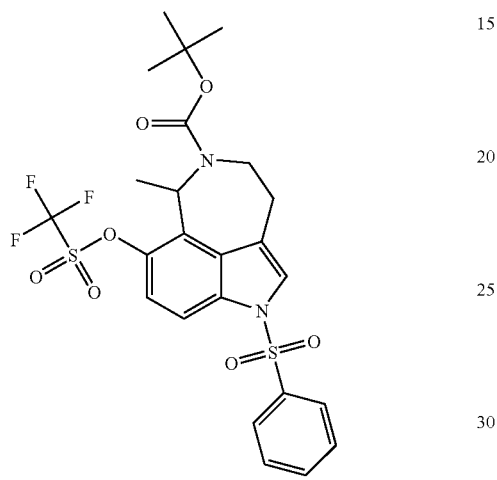

tert-butyl 7-hydroxy-6-methyl-1-(phenylsulfonyl)-1,3,4,6-tetrahydro-5H-azepino[5,4,3-cd]indole-5-carboxylate, Intermediate 15 (80 mg, 0.18 mmol), N-phenyltrifluoromethansulfonimide (129 mg, 0.36 mmol) DCM (3 mL) and N,N-diisopropylethylamine (DIPEA) (70 mg, 0.54 mmol) were mixed into a 16 mm test tube with screw cap. The reaction mixture was stirred at room temperature over night, an additional equivalent of N-phenyltrifluoromethansulfonimide and DIPEA was added together with more DCM (6 mL) and the turbid mixture was stirred for another two days. The clear solution was washed with acidic (pH<1, HCl) ice water and brine. The solvent was evaporated at reduced pressure and the resulting solid was triturated with a minute amount of cold MeOH (1 mL). White crystals were filtered off and dried to give 60 mg of product. MS m/z 519 [M+H-isobutene]$^+$.

EXAMPLE 19

6-Methyl-1-(phenylsulfonyl)-3,4,5,6-tetrahydro-1H-azepino[5,4,3-cd]indol-7-yl trifluoromethanesulfonate trifluoroacetate

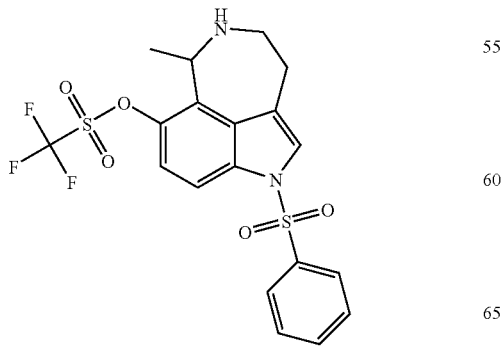

tert-Butyl 6-methyl-1-(phenylsulfonyl)-7-{[(trifluoromethyl)sulfonyl]oxy}-1,3,4,6-tetrahydro-5H-azepino[5,4,3-cd]indole-5-carboxylate, Intermediate 16 (12.6 mg, 0.022 mmol) was dissolved in a 50/50 mixture of DCM/TFA (1 mL) and left at room temperature for one hour. The evaporated crude product was purified by preparative HPLC (ACE C8 5 mm, water containing 0.1% TFA —CH3CN) to give 7.2 mg of the title compound as a light brown oil. MS m/z 474 [M+H]$^+$.

EXAMPLE 20

7-Methoxy-5,6-dimethyl-α-(phenylsulfonyl)-3,4,5,6-tetrahydro-3H-azepino[5,4,3-cd]indole

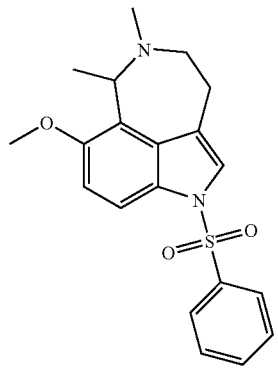

To 7-Methoxy-6-methyl-1-(phenylsulfonyl)-3,4,5,6-tetrahydro-1H-azepino[5,4,3-cd]indole, Example 17, (11.4 mg, 0.032 mmol) in DCE (2 mL) was added sodium triacetoxy borohydride (20 mg, 0.096 mmol) followed by a drop of aq. conc. formaldehyde (11 mg, 0.10 mmol) and the mixture was stirred at 40° C. for one hour. The organic phase was washed twice with 0.1 M NaOH and the oil from the evaporated organic phase was purified by preparative HPLC (Xterra C18, 10 mM NH4CO3 (pH 10)-CH3CN) to give 7.5 mg of the title compound as an off white oil. MS m/z 371 [M+H]$^+$.

EXAMPLE 21

7-Ethoxy-6-methyl-1-(phenylsulfonyl)-3,4,5,6-tetrahydro-1H-azepino[5,4,3-cd]indole

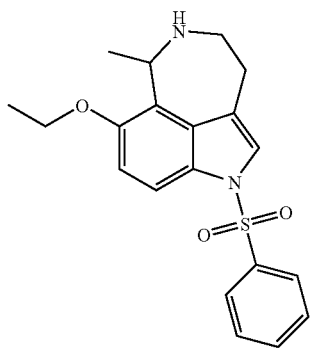

tert-Butyl 7-hydroxy-6-methyl-1-(phenylsulfonyl)-1,3,4,6-tetrahydro-5H-azepino[5,4,3-cd]indole-5-carboxylate, Intermediate 15 (16 mg, 0.036 mmol), acetone (5 mL), K₂CO₃ (50 mg, 0.36 mmol) and EtI (34 mg, 0.22 mmol) were added into a 16 mm test tube with screw cap and the suspension was stirred at 62° C. over night. The solvent from the filtered mixture was evaporated at reduced pressure and the residue was dissolved in DCM/TFA 50/50 (1 mL) and left in room temperature for two hours. The solvent was evaporated at reduced pressure and the crude was purified by preparative HPLC (Xterra C18, 10 mM NH4CO3 (pH 10)-CH3CN) to give 9.0 mg (67%) of the title compound as a brown oil. MS m/z 371 [M+H]⁺.

General Procedure for Sulfonylation Used in Example 22-Example 70:

NaH (95%; ca. 3 mg, 0.125 mmol, 2.5 eq) was added to a slurry of tert-butyl 1,3,4,6-tetrahydro-5H-azepino[5,4,3-cd]indole-5-carboxylate, Intermediate 12 (14 mg, 0.050 mmol) in dry CH₃CN (350 μL). The vial was immediately flushed with N₂, sealed and agitated at room temperature for 1.5 h. To the reaction mixture was added (through the septum) a solution of the sulfonyl chloride (0.75 mmol, 1.5 eq) dissolved in dry CH₃CN (150 μL) and the agitation was continued for 3 h. TFA (100 μL) was added to the reaction mixture giving the deprotected product after 2-16 h reaction time. The reaction mix was diluted with H₂O (100 μL) and MeOH (ca.1000 μL), and was purified by preparative reverse phase HPLC (ACE C₈, 5 μm 21×50 mm, flow 25 ml/min, 0.1% TFA in MilliQ H₂O—CH₃CN) to give the product as the corresponding trifluoroacetate salt. Sulfonyl chlorides which were not soluble in CH₃CN were added directly to the reaction mixtures as solids.

EXAMPLE 22

1-[(2-Chloro-6-methylphenyl)sulfonyl]-3,4,5,6-tetrahydro-1H-azepino[5,4,3-cd]indole trifluoroacetate

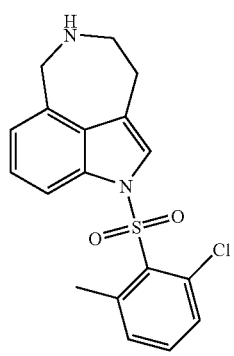

The title compound was prepared from tert-butyl 1,3,4,6-tetrahydro-5H-azepino[5,4,3-cd]indole-5-carboxylate, Intermediate 12 (14 mg, 0.05 mmol) and 2-chloro-6-methylbenzenesulfonyl chloride (17 mg, 0.75 mmol) as described in the general procedure above, to give 13.3 mg of product. MS (ESI) m/z 361 [M+H]⁺.

EXAMPLE 23

1-[(3-Chloro-2-methylphenyl)sulfonyl]-3,4,5,6-tetrahydro-1H-azepino[5,4,3-cd]indole trifluoroacetate

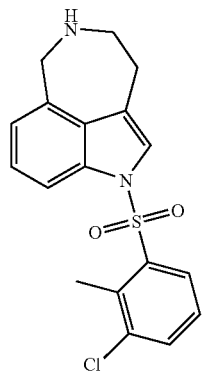

The title compound was prepared from tert-butyl 1,3,4,6-tetrahydro-5H-azepino[5,4,3-cd]indole-5-carboxylate, Intermediate 12 (14 mg, 0.05 mmol) and 3-chloro-2-methylbenzenesulfonyl chloride (17 mg, 0.75 mmol) as described in the general procedure above, to give 5.2 mg of product. MS (ESI) m/z 361 [M+H]⁺.

EXAMPLE 24

1-[(3-Chloro-4-fluorophenyl)sulfonyl]-3,4,5,6-tetrahydro-1H-azepino[5,4,3-cd]indole trifluoroacetate

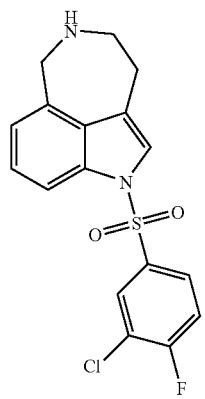

The title compound was prepared from tert-butyl 1,3,4,6-tetrahydro-5H-azepino[5,4,3-cd]indole-5-carboxylate, Intermediate 12 (14 mg, 0.05 mmol) and 3-chloro-4-fluorobenzenesulfonyl chloride (17 mg, 0.75 mmol) as described in the general procedure above, to give 10.1 mg of product. MS (ESI) m/z 365 [M+H]⁺.

EXAMPLE 25

1-[(2-Chlorophenyl)sulfonyl]-3,4,5,6-tetrahydro-1H-azepino[5,4,3-cd]indole trifluoroacetate

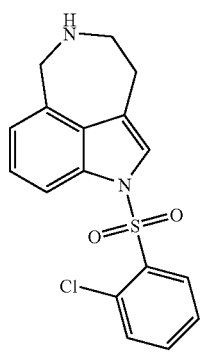

The title compound was prepared from tert-butyl 1,3,4,6-tetrahydro-5H-azepino[5,4,3-cd]indole-5-carboxylate, Intermediate 12 (14 mg, 0.05 mmol) and 2-chlorobenzenesulfonyl chloride (16 mg, 0.75 mmol) as described in the general procedure above, to give 11.7 mg of product. MS (ESI) m/z 347 [M+H]$^+$.

EXAMPLE 26

1-[(3-Chlorophenyl)sulfonyl]-3,4,5,6-tetrahydro-1H-azepino[5,4,3-cd]indole trifluoroacetate

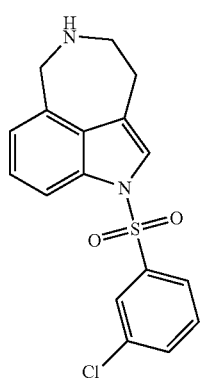

The title compound was prepared from tert-butyl 1,3,4,6-tetrahydro-5H-azepino[5,4,3-cd]indole-5-carboxylate, Intermediate 12 (14 mg, 0.05 mmol) and 3-chlorobenzenesulfonyl chloride (16 mg, 0.75 mmol) as described in the general procedure above, to give 1.2 mg of product. MS (ESI) m/z 347 [M+H]$^+$.

EXAMPLE 27

1-[(4-Chlorophenyl)sulfonyl]-3,4,5,6-tetrahydro-1H-azepino[5,4,3-cd]indole trifluoroacetate

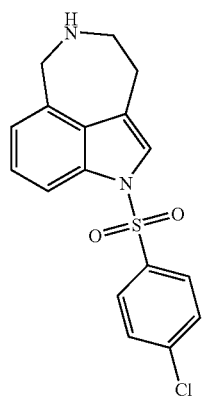

The title compound was prepared from tert-butyl 1,3,4,6-tetrahydro-5H-azepino[5,4,3-cd]indole-5-carboxylate, Intermediate 12 (14 mg, 0.05 mmol) and 4-chlorobenzenesulfonyl chloride (16 mg, 0.75 mmol) as described in the general procedure above, to give 13.1 mg of product. MS (ESI) m/z 347 [M+H]$^+$.

EXAMPLE 28

1-[(3-Fluorophenyl)sulfonyl]-3,4,5,6-tetrahydro-1H-azepino[5,4,3-cd]indole trifluoroacetate

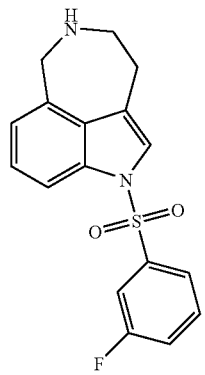

The title compound was prepared from tert-butyl 1,3,4,6-tetrahydro-5H-azepino[5,4,3-cd]indole-5-carboxylate, Intermediate 12 (14 mg, 0.05 mmol) and 3-fluorobenzenesulfonyl chloride (15 mg, 0.75 mmol) as described in the general procedure above, to give 9.7 mg of product. MS (ESI) m/z 331 [M+H]$^+$.

EXAMPLE 29

1-[(4-Fluorophenyl)sulfonyl]-3,4,5,6-tetrahydro-1H-azepino[5,4,3-cd]indole trifluoroacetate

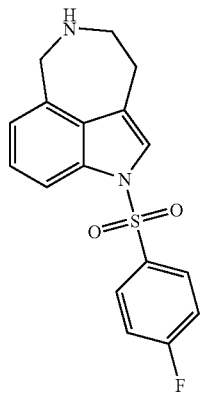

The title compound was prepared from tert-butyl 1,3,4,6-tetrahydro-5H-azepino[5,4,3-cd]indole-5-carboxylate, Intermediate 12 (14 mg, 0.05 mmol) and 4-fluorobenzenesulfonyl chloride (15 mg, 0.75 mmol) as described in the general procedure above, to give 12.0 mg of product. MS (ESI) m/z 331 [M+H]$^+$.

EXAMPLE 30

1-[(2,6-Difluorophenyl)sulfonyl]-3,4,5,6-tetrahydro-1H-azepino[5,4,3-cd]indole trifluoroacetate

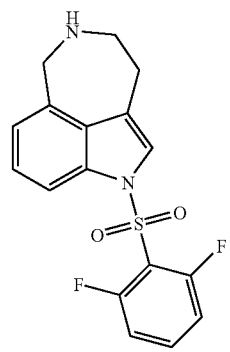

The title compound was prepared from tert-butyl 1,3,4,6-tetrahydro-5H-azepino[5,4,3-cd]indole-5-carboxylate, Intermediate 12 (14 mg, 0.05 mmol) and 2,6-difluorobenzenesulfonyl chloride (16 mg, 0.75 mmol) as described in the general procedure above, to give 10.8 mg of product. MS (ESI) m/z 349 [M+H]$^+$.

EXAMPLE 31

1-[(2,5-Difluorophenyl)sulfonyl]-3,4,5,6-tetrahydro-1H-azepino[5,4,3-cd]indole trifluoroacetate

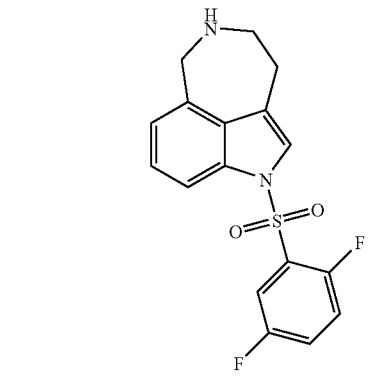

The title compound was prepared from tert-butyl 1,3,4,6-tetrahydro-5H-azepino[5,4,3-cd]indole-5-carboxylate, Intermediate 12 (14 mg, 0.05 mmol) and 2,5-difluorobenzenesulfonyl chloride (16 mg, 0.75 mmol) as described in the general procedure above, to give 9.4 mg of product. MS (ESI) m/z 349 [M+H]$^+$.

EXAMPLE 32

1-[(3,5-Difluorophenyl)sulfonyl]-3,4,5,6-tetrahydro-1H-azepino[5,4,3-cd]indole trifluoroacetate

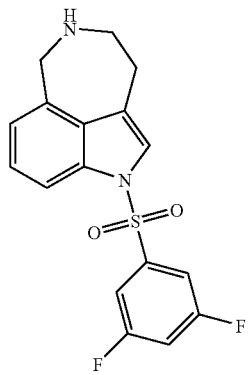

The title compound was prepared from tert-butyl 1,3,4,6-tetrahydro-5H-azepino[5,4,3-cd]indole-5-carboxylate, Intermediate 12 (14 mg, 0.05 mmol) and 3,5-difluorobenzenesulfonyl chloride (16 mg, 0.75 mmol) as described in the general procedure above, to give 9.9 mg of product. MS (ESI) m/z 349 [M+H]$^+$.

EXAMPLE 33

1-[(2,4-Difluorophenyl)sulfonyl]-3,4,5,6-tetrahydro-1H-azepino[5,4,3-cd]indole trifluoroacetate

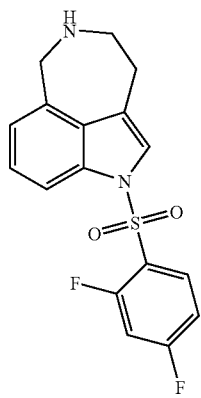

The title compound was prepared from tert-butyl 1,3,4,6-tetrahydro-5H-azepino[5,4,3-cd]indole-5-carboxylate, Intermediate 12 (14 mg, 0.05 mmol) and 2,4-difluorobenzenesulfonyl chloride (16 mg, 0.75 mmol) as described in the general procedure above, to give 9.6 mg of product. MS (ESI) m/z 349 [M+H]$^+$.

EXAMPLE 34

1-[(3,4-Difluorophenyl)sulfonyl]-3,4,5,6-tetrahydro-1H-azepino[5,4,3-cd]indole trifluoroacetate

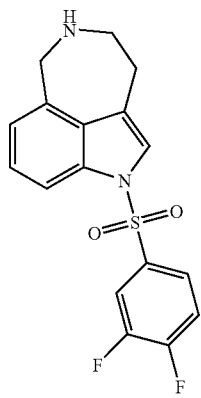

The title compound was prepared from tert-butyl 1,3,4,6-tetrahydro-5H-azepino[5,4,3-cd]indole-5-carboxylate, Intermediate 12 (14 mg, 0.05 mmol) and 3,4-difluorobenzenesulfonyl chloride (16 mg, 0.75 mmol) as described in the general procedure above, to give 7.4 mg (32%) of product. MS (ESI) m/z 349 [M+H]$^+$.

EXAMPLE 35

1-[(2-Methylphenyl)sulfonyl]-3,4,5,6-tetrahydro-1H-azepino[5,4,3-cd]indole trifluoroacetate

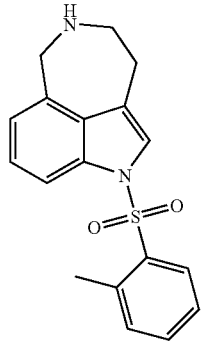

The title compound was prepared from tert-butyl 1,3,4,6-tetrahydro-5H-azepino[5,4,3-cd]indole-5-carboxylate, Intermediate 12 (14 mg, 0.05 mmol) and 2-methylbenzenesulfonyl chloride (14 mg, 0.75 mmol) as described in the general procedure above, to give 8.2 mg of product. MS (ESI) m/z 327 [M+H]$^+$.

EXAMPLE 36

1-[(4-methylphenyl)sulfonyl]-3,4,5,6-tetrahydro-1H-azepino[5,4,3-cd]indole trifluoroacetate

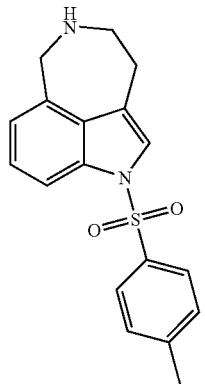

The title compound was prepared from tert-butyl 1,3,4,6-tetrahydro-5H-azepino[5,4,3-cd]indole-5-carboxylate, Intermediate 12 (14 mg, 0.05 mmol) and 4-methylbenzenesulfonyl chloride (14 mg, 0.75 mmol) as described in the general procedure above, to give 12.5 mg of product. MS (ESI) m/z 327 [M+H]$^+$.

EXAMPLE 37

1-[(2,5-Dimethyl-3-thienyl)sulfonyl]-3,4,5,6-tetrahydro-1H-azepino[5,4,3-cd]indole trifluoroacetate

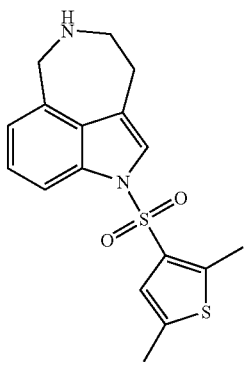

The title compound was prepared from tert-butyl 1,3,4,6-tetrahydro-5H-azepino[5,4,3-cd]indole-5-carboxylate, Intermediate 12 (14 mg, 0.05 mmol) and 2,5-dimethylthiophene-3-sulfonyl chloride (16 mg, 0.75 mmol) as described in the general procedure above, to give 9.8 mg of product. MS (ESI) m/z 347 [M+H]$^+$.

EXAMPLE 38

1-[(2,5-Dimethylphenyl)sulfonyl]-3,4,5,6-tetrahydro-1H-azepino[5,4,3-cd]indole trifluoroacetate

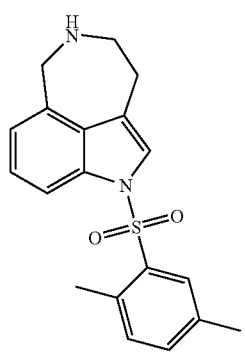

The title compound was prepared from tert-butyl 1,3,4,6-tetrahydro-5H-azepino[5,4,3-cd]indole-5-carboxylate, Intermediate 12 (14 mg, 0.05 mmol) and 2,5-dimethylbenzenesulfonyl chloride (15 mg, 0.75 mmol) as described in the general procedure above, to give 12.1 mg of product. MS (ESI) m/z 341 [M+H]$^+$.

EXAMPLE 39

1-[(3,5-Dimethylphenyl)sulfonyl]-3,4,5,6-tetrahydro-1H-azepino[5,4,3-cd]indole hydrochloride

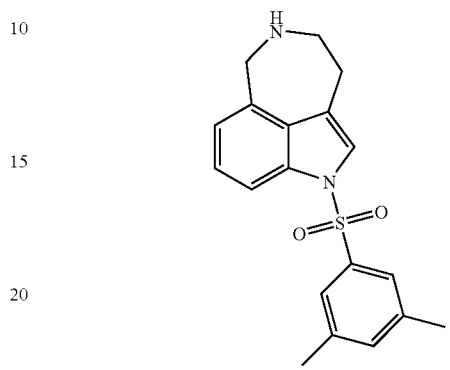

The title compound was prepared from tert-butyl 1,3,4,6-tetrahydro-5H-azepino[5,4,3-cd]indole-5-carboxylate, Intermediate 12 (14 mg, 0.05 mmol) and 3,5-dimethylbenzenesulfonyl chloride (15 mg, 0.75 mmol) as described in the general procedure above, to give 8.9 mg of product. MS (ESI) m/z 341 [M+H]$^+$.

EXAMPLE 40

1-{[4-fluoro-3-(trifluoromethyl)phenyl]sulfonyl}-3,4,5,6-tetrahydro-1H-azepino[5,4,3-cd] in dole trifluoro acetate

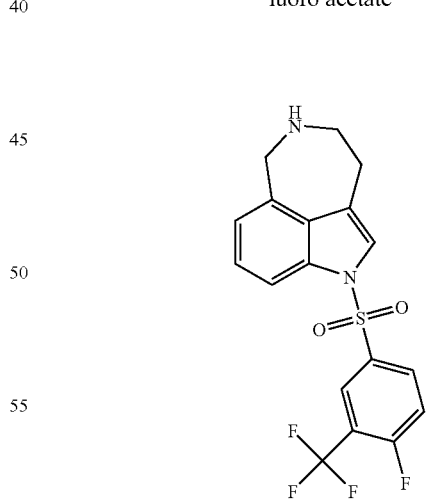

The title compound was prepared from tert-butyl 1,3,4,6-tetrahydro-5H-azepino[5,4,3-cd]indole-5-carboxylate, Intermediate 12 (14 mg, 0.05 mmol) and 4-fluoro-3-(trifluoromethyl)benzenesulfonyl chloride (20 mg, 0.75 mmol) as described in the general procedure above, to give 10.3 mg of product. MS (ESI) m/z 399 [M+H]$^+$.

EXAMPLE 41

1-(1-Benzofuran-2-ylsulfonyl)-3,4,5,6-tetrahydro-1H-azepino[5,4,3-cd]indole trifluoroacetate

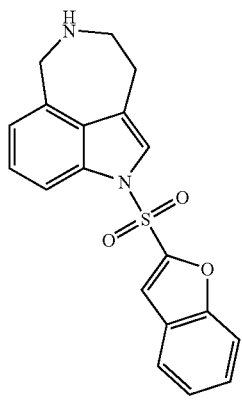

The title compound was prepared from tert-butyl 1,3,4,6-tetrahydro-5H-azepino[5,4,3-cd]indole-5-carboxylate, Intermediate 12 (14 mg, 0.05 mmol) and 1-benzofuran-2-sulfonyl chloride (16 mg, 0.75 mmol) as described in the general procedure above, to give 3.6 mg of product. MS (ESI) m/z 353 [M+H]$^+$.

EXAMPLE 42

1-(1,3-Benzothiazol-6-ylsulfonyl)-3,4,5,6-tetrahydro-1H-azepino[5,4,3-cd]indole trifluoroacetate

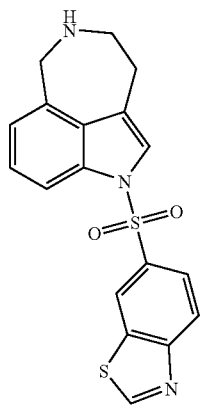

The title compound was prepared from tert-butyl 1,3,4,6-tetrahydro-5H-azepino[5,4,3-cd]indole-5-carboxylate, Intermediate 12 (14 mg, 0.05 mmol) and 1,3-benzothiazole-6-sulfonyl chloride (18 mg, 0.75 mmol) as described in the general procedure above, to give 3.6 mg of product. MS (ESI) m/z 370 [M+H]$^+$.

EXAMPLE 43

1-[(1-Methyl-1H-imidazol-4-yl)sulfonyl]-3,4,5,6-tetrahydro-1H-azepino[5,4,3-cd]indole trifluoroacetate

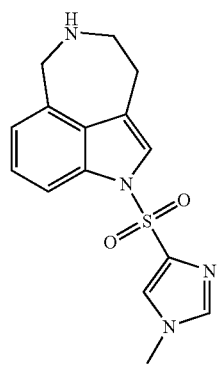

The title compound was prepared from tert-butyl 1,3,4,6-tetrahydro-5H-azepino[5,4,3-cd]indole-5-carboxylate, Intermediate 12 (14 mg, 0.05 mmol) and 1-methyl-1H-imidazole-4-sulfonyl chloride (14 mg, 0.75 mmol) as described in the general procedure above, to give 11.0 mg of product. MS (ESI) m/z 317 [M+H]$^+$.

EXAMPLE 44

1-[(6-Chloroimidazo[2,1-b][1,3]thiazol-5-yl)sulfonyl]-3,4,5,6-tetrahydro-1H-azepino[5,4,3-cd]indole trifluoroacetate

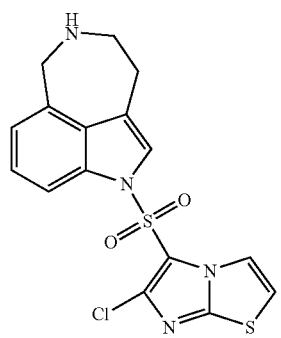

The title compound was prepared from tert-butyl 1,3,4,6-tetrahydro-5H-azepino[5,4,3-cd]indole-5-carboxylate, Intermediate 12 (14 mg, 0.05 mmol) and 6-chloroimidazo[2,1-b][1,3]thiazole-5-sulfonyl chloride (19 mg, 0.75 mmol) as described in the general procedure above, to give 3.9 mg of product. MS (ESI) m/z 393 [M+H]$^+$.

EXAMPLE 45

1-{[2-(Trifluoromethyl)phenyl]sulfonyl}-3,4,5,6-tetrahydro-1H-azepino[5,4,3-cd]indole trifluoroacetate

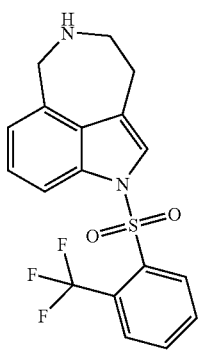

The title compound was prepared from tert-butyl 1,3,4,6-tetrahydro-5H-azepino[5,4,3-cd]indole-5-carboxylate, Intermediate 12 (14 mg, 0.05 mmol) and 2-(trifluoromethyl)benzenesulfonyl chloride (18 mg, 0.75 mmol) as described in the general procedure above, to give 1.9 mg of product. MS (ESI) m/z 381 [M+H]+.

EXAMPLE 46

1-(1-Benzothien-2-ylsulfonyl)-3,4,5,6-tetrahydro-1H-azepino[5,4,3-cd]indole trifluoroacetate

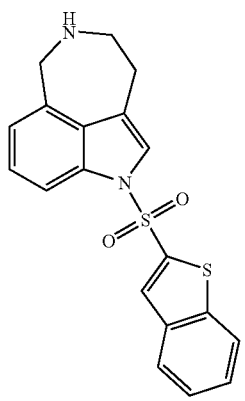

The title compound was prepared from tert-butyl 1,3,4,6-tetrahydro-5H-azepino[5,4,3-cd]indole-5-carboxylate, Intermediate 12 (14 mg, 0.05 mmol) and 1-benzothiophene-2-sulfonyl chloride (18 mg, 0.75 mmol) as described in the general procedure above, to give 9.9 mg of product. MS (ESI) m/z 369 [M+H]+.

EXAMPLE 47

1-[(5-Fluoro-2-methylphenyl)sulfonyl]-3,4,5,6-tetrahydro-1H-azepino[5,4,3-cd]indole trifluoroacetate

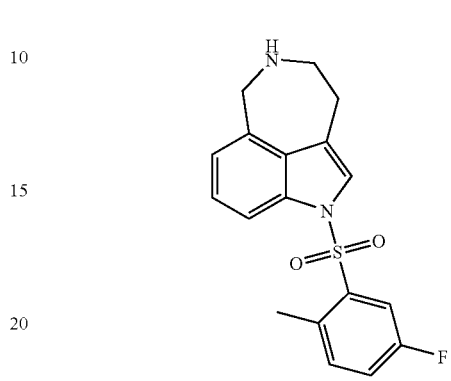

The title compound was prepared from tert-butyl 1,3,4,6-tetrahydro-5H-azepino[5,4,3-cd]indole-5-carboxylate, Intermediate 12 (14 mg, 0.05 mmol) and 5-fluoro-2-methylbenzenesulfonyl chloride (16 mg, 0.75 mmol) as described in the general procedure above, to give 14.5 mg of product. MS (ESI) m/z 345 [M+H]+.

EXAMPLE 48

1-{[4-(Trifluoromethyl)phenyl]sulfonyl}-3,4,5,6-tetrahydro-1H-azepino[5,4,3-cd]indole trifluoroacetate

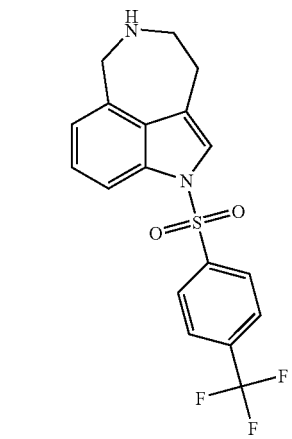

The title compound was prepared from tert-butyl 1,3,4,6-tetrahydro-5H-azepino[5,4,3-cd]indole-5-carboxylate, Intermediate 12 (14 mg, 0.05 mmol) and 4-trifluoromethyl benzenesulfonyl chloride (18 mg, 0.75 mmol) as described in the general procedure above, to give 13.9 mg of product. MS (ESI) m/z 381 [M+H]+.

EXAMPLE 49

4-Methyl-2-(3,4,5,6-tetrahydro-1H-azepino[5,4,3-cd]indol-1-ylsulfonyl)benzonitrile trifluoroacetate

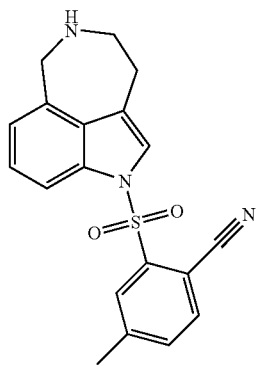

The title compound was prepared from tert-butyl 1,3,4,6-tetrahydro-5H-azepino[5,4,3-cd]indole-5-carboxylate, Intermediate 12 (14 mg, 0.05 mmol) and 2-cyano-5-methylbenzenesulfonyl chloride (16 mg, 0.75 mmol) as described in the general procedure above, to give 1.3 mg of product. MS (ESI) m/z 352 [M+H]$^+$.

EXAMPLE 50

1-[(4,5-Dichloro-2-thienyl)sulfonyl]-3,4,5,6-tetrahydro-1H-azepino[5,4,3-cd]indole trifluoroacetate

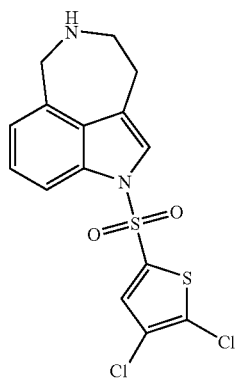

The title compound was prepared from tert-butyl 1,3,4,6-tetrahydro-5H-azepino[5,4,3-cd]indole-5-carboxylate, Intermediate 12 (14 mg, 0.05 mmol) and 4,5-dichlorothiophene-2-sulfonyl chloride (19 mg, 0.75 mmol) as described in the general procedure above, to give 4.0 mg of product. MS (ESI) m/z 387 [M+H]$^+$.

EXAMPLE 51

1-[(4-tert-Butylphenyl)sulfonyl]-3,4,5,6-tetrahydro-1H-azepino[5,4,3-cd]indole trifluoroacetate

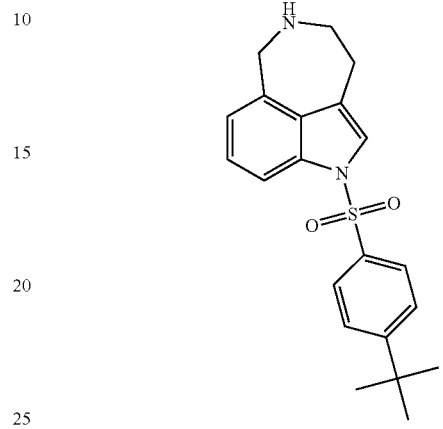

The title compound was prepared from tert-butyl 1,3,4,6-tetrahydro-5H-azepino[5,4,3-cd]indole-5-carboxylate, Intermediate 12 (14 mg, 0.05 mmol) and 4-tert-butylbenzenesulfonyl chloride (18 mg, 0.75 mmol) as described in the general procedure above, to give 13.1 mg of product. MS (ESI) m/z 369 [M+H]$^+$.

EXAMPLE 52

1-[(2,5-Dimethyl-3-furyl)sulfonyl]-3,4,5,6-tetrahydro-1H-azepino[5,4,3-cd]indole trifluoroacetate

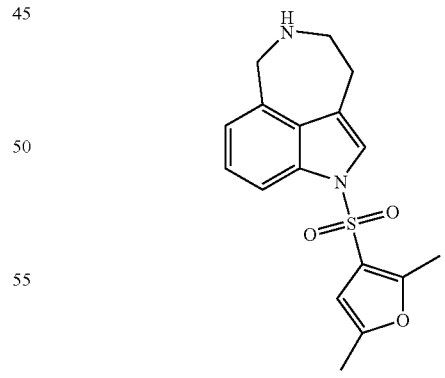

The title compound was prepared from tert-butyl 1,3,4,6-tetrahydro-5H-azepino[5,4,3-cd]indole-5-carboxylate, Intermediate 12 (14 mg, 0.05 mmol) and 2,5-dimethylfuran-3-sulfonyl chloride (15 mg, 0.75 mmol) as described in the general procedure above, to give 11.6 mg of product. MS (ESI) m/z 331 [M+H]$^+$.

EXAMPLE 53

1-[(2,4-Dimethyl-1,3-thiazol-5-yl)sulfonyl]-3,4,5,6-tetrahydro-1H-azepino[5,4,3-cd]indole trifluoroacetate

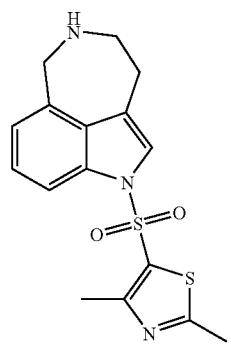

The title compound was prepared from tert-butyl 1,3,4,6-tetrahydro-5H-azepino[5,4,3-cd]indole-5-carboxylate, Intermediate 12 (14 mg, 0.05 mmol) and 2,4-dimethyl-1,3-thiazole-5-sulfonyl chloride (16 mg, 0.75 mmol) as described in the general procedure above, to give 6.1 mg of product. MS (ESI) m/z 348 [M+H]$^+$.

EXAMPLE 54

1-[(3,5-Dimethylisoxazol-4-yl)sulfonyl]-3,4,5,6-tetrahydro-1H-azepino[5,4,3-cd]indole trifluoroacetate

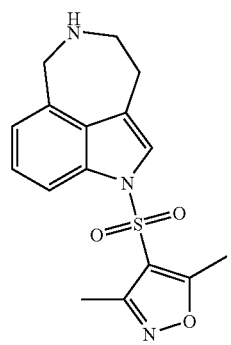

The title compound was prepared from tert-butyl 1,3,4,6-tetrahydro-5H-azepino[5,4,3-cd]indole-5-carboxylate, Intermediate 12 (14 mg, 0.05 mmol) and 3,5-dimethylisoxazole-4-sulfonyl chloride (15 mg, 0.75 mmol) as described in the general procedure above, to give 7.9 mg of product. MS (ESI) m/z 332 [M+H]$^+$.

EXAMPLE 55

1-[(5-Chloro-2-thienyl)sulfonyl]-3,4,5,6-tetrahydro-1H-azepino[5,4,3-cd]indole trifluoroacetate

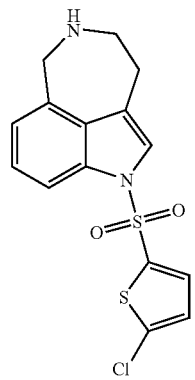

The title compound was prepared from tert-butyl 1,3,4,6-tetrahydro-5H-azepino[5,4,3-cd]indole-5-carboxylate, Intermediate 12 (14 mg, 0.05 mmol) and 5-chlorothiophene-2-sulfonyl chloride (16 mg, 0.75 mmol) as described in the general procedure above, to give 5.7 mg of product. MS (ESI) m/z 353 [M+H]$^+$.

EXAMPLE 56

4-(3,4,5,6-Tetrahydro-1H-azepino[5,4,3-cd]indol-1-ylsulfonyl)benzonitrile trifluoroacetate

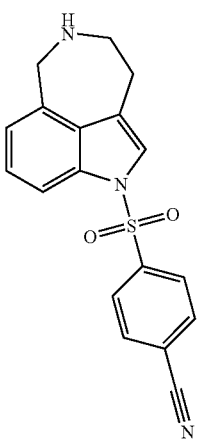

The title compound was prepared from tert-butyl 1,3,4,6-tetrahydro-5H-azepino[5,4,3-cd]indole-5-carboxylate, Intermediate 12 (14 mg, 0.05 mmol) and 4-cyanobenzenesulfonyl chloride (15 mg, 0.75 mmol) as described in the general procedure above, to give 6.4 mg of product. MS (ESI) m/z 338 [M+H]$^+$.

EXAMPLE 57

3-(3,4,5,6-Tetrahydro-1H-azepino[5,4,3-cd]indol-1-ylsulfonyl)benzonitrile trifluoroacetate

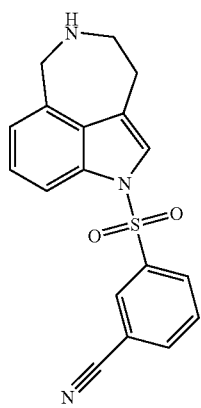

The title compound was prepared from tert-butyl 1,3,4,6-tetrahydro-5H-azepino[5,4,3-cd]indole-5-carboxylate, Intermediate 12 (14 mg, 0.05 mmol) and 3-cyanobenzenesulfonyl chloride (15 mg, 0.75 mmol) as described in the general procedure above, to give 10.1 mg of product. MS (ESI) m/z 338 [M+H]$^+$.

EXAMPLE 58

1-[(4-Methoxyphenyl)sulfonyl]-3,4,5,6-tetrahydro-1H-azepino[5,4,3-cd]indole trifluoroacetate

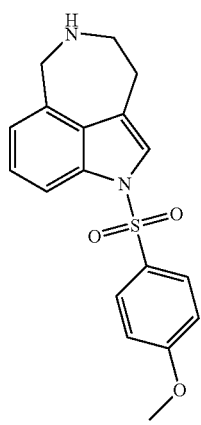

The title compound was prepared from tert-butyl 1,3,4,6-tetrahydro-5H-azepino[5,4,3-cd]indole-5-carboxylate, Intermediate 12 (14 mg, 0.05 mmol) and 4-methoxybenzenesulfonyl chloride (16 mg, 0.75 mmol) as described in the general procedure above, to give 12.3 mg of product. MS (ESI) m/z 343 [M+H]$^+$.

EXAMPLE 59

1-[(2-Methoxy-6-methylphenyl)sulfonyl]-3,4,5,6-tetrahydro-1H-azepino[5,4,3-cd]indole trifluoroacetate

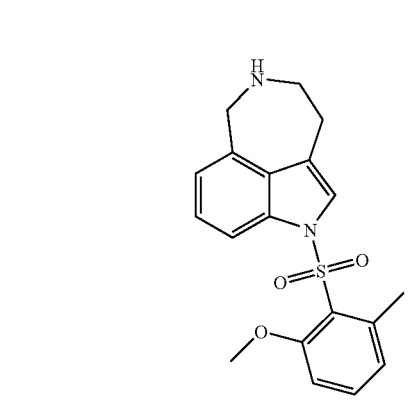

The title compound was prepared from tert-butyl 1,3,4,6-tetrahydro-5H-azepino[5,4,3-cd]indole-5-carboxylate, Intermediate 12 (14 mg, 0.05 mmol) and 2-methoxy-6-methylbenzenesulfonyl chloride (17 mg, 0.75 mmol) as described in the general procedure above, to give 6.4 mg of product. MS (ESI) m/z 357 [M+H]$^+$.

EXAMPLE 60

1-[(2-Methoxy-5-methylphenyl)sulfonyl]-3,4,5,6-tetrahydro-1H-azepino[5,4,3-cd]indole trifluoroacetate

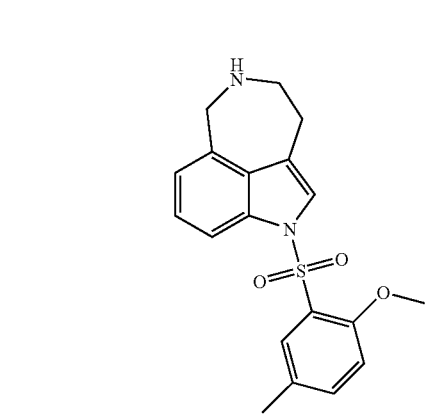

The title compound was prepared from tert-butyl 1,3,4,6-tetrahydro-5H-azepino[5,4,3-cd]indole-5-carboxylate, Intermediate 12 (14 mg, 0.05 mmol) and 2-methoxy-5-methylbenzenesulfonyl chloride (17 mg, 0.75 mmol) as described in the general procedure above, to give 3.6 mg of product. MS (ESI) m/z 357 [M+H]$^+$.

EXAMPLE 61

1-[(2-methoxy-4-methylphenyl)sulfonyl]-3,4,5,6-tetrahydro-1H-azepino[5,4,3-cd]indole trifluoroacetate

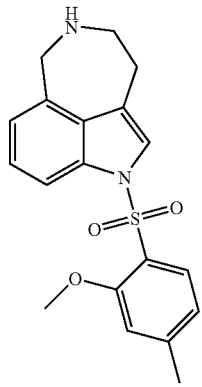

The title compound was prepared from tert-butyl 1,3,4,6-tetrahydro-5H-azepino[5,4,3-cd]indole-5-carboxylate, Intermediate 12 (14 mg, 0.05 mmol) and 2-methoxy-4-methylbenzenesulfonyl chloride (17 mg, 0.75 mmol) as described in the general procedure above, to give 17.4 mg of product. MS (ESI) m/z 357 [M+H]$^+$.

EXAMPLE 62

1-(1-Benzothien-3-ylsulfonyl)-3,4,5,6-tetrahydro-1H-azepino[5,4,3-cd]indole trifluoroacetate

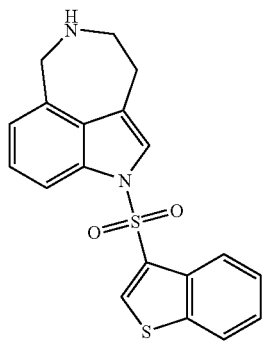

The title compound was prepared from tert-butyl 1,3,4,6-tetrahydro-5H-azepino[5,4,3-cd]indole-5-carboxylate, Intermediate 12 (14 mg, 0.05 mmol) and 1-benzothiophene-3-sulfonyl chloride (18 mg, 0.75 mmol) as described in the general procedure above, to give 5.2 mg of product. MS (ESI) m/z 369 [M+H]$^+$.

EXAMPLE 63

1-[(4-Isopropylphenyl)sulfonyl]-3,4,5,6-tetrahydro-1H-azepino[5,4,3-cd]indole trifluoroacetate

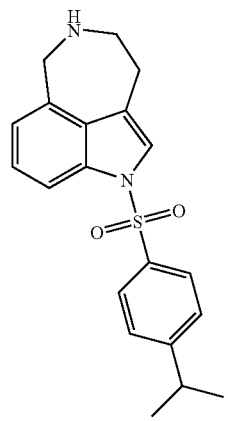

The title compound was prepared from tert-butyl 1,3,4,6-tetrahydro-5H-azepino[5,4,3-cd]indole-5-carboxylate, Intermediate 12 (14 mg, 0.05 mmol) and 4-isopropylbenzenesulfonyl chloride (16 mg, 0.75 mmol) as described in the general procedure above, to give 9.5 mg of product. The NMR spectrum contains signals from what seems to be two regioisomers in a ratio of 3:1. MS (ESI) m/z 355 [M+H]$^+$.

EXAMPLE 64

1-[(4-Propylphenyl)sulfonyl]-3,4,5,6-tetrahydro-1H-azepino[5,4,3-cd]indole trifluoroacetate

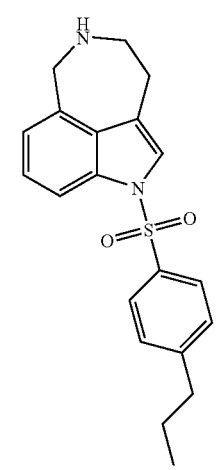

The title compound was prepared from tert-butyl 1,3,4,6-tetrahydro-5H-azepino[5,4,3-cd]indole-5-carboxylate, Intermediate 12 (14 mg, 0.05 mmol) and 4-n-propylbenzenesulfonyl chloride (16 mg, 0.75 mmol) as described in the general procedure above, to give 8.9 mg of product. MS (ESI) m/z 355 [M+H]$^+$.

EXAMPLE 65

1-[(5-Ethyl-2-methoxyphenyl)sulfonyl]-3,4,5,6-tetrahydro-1H-azepino[5,4,3-cd]indole trifluoroacetate

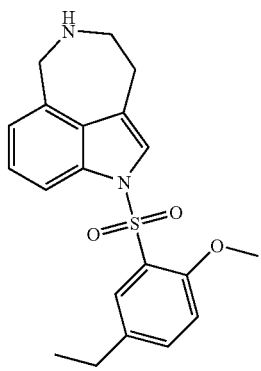

The title compound was prepared from tert-butyl 1,3,4,6-tetrahydro-5H-azepino[5,4,3-cd]indole-5-carboxylate, Intermediate 12. (14 mg, 0.05 mmol) and 5-ethyl-2-methoxybenzenesulfonyl chloride (18 mg, 0.75 mmol) as described in the general procedure above, to give 9.1 mg of product. MS (ESI) m/z 371 [M+H]$^+$.

EXAMPLE 66

1-[(5-Bromo-2,3-dihydro-1-benzofuran-7-yl)sulfonyl]-3,4,5,6-tetrahydro-H-azepino[5,4,3-cd]indole trifluoroacetate

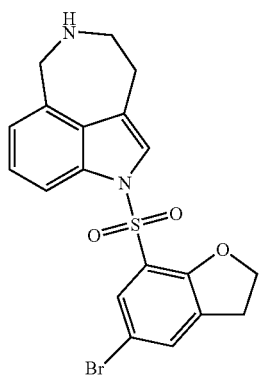

The title compound was prepared from tert-butyl 1,3,4,6-tetrahydro-5H-azepino[5,4,3-cd]indole-5-carboxylate, Intermediate 12 (14 mg, 0.05 mmol) and 5-bromo-2,3-dihydro-1-benzofuran-7-sulfonyl chloride (22 mg, 0.75 mmol) as described in the general procedure above, to give 3.9 mg of product. MS (ESI) m/z 433 [M+H]$^+$.

EXAMPLE 67

1-[(5-Chloro-3-methyl-1-benzothien-2-yl)sulfonyl]-3,4,5,6-tetrahydro-1H-azepino[5,4,3-cd]indole trifluoroacetate

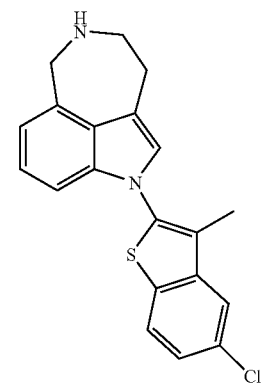

The title compound was prepared from tert-butyl 1,3,4,6-tetrahydro-5H-azepino[5,4,3-cd]indole-5-carboxylate, Intermediate 12 (14 mg, 0.05 mmol) and 5-chloro-3-methyl-1-benzothiophene-2-sulfonyl chloride (21 mg, 0.75 mmol) as described in the general procedure above, to give 4.2 mg of product. MS (ESI) m/z 417 [M+H]$^+$.

EXAMPLE 68

1-[(2-Ethoxy-5-isopropylphenyl)sulfonyl]-3,4,5,6-tetrahydro-1H-azepino[5,4,3-cd]indole trifluoroacetate

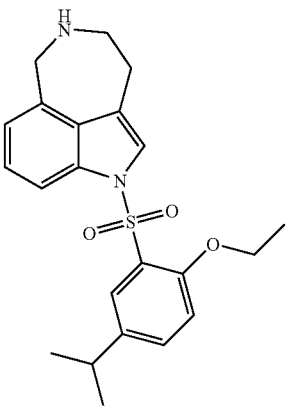

The title compound was prepared from tert-butyl 1,3,4,6-tetrahydro-5H-azepino[5,4,3-cd]indole-5-carboxylate, Intermediate 12 (14 mg, 0.05 mmol) and 2-ethoxy-5-isopropylbenzenesulfonyl chloride (20 mg, 0.75 mmol) as described in the general procedure above, to give 14.5 mg of product. MS (ESI) m/z 399 [M+H]$^+$.

EXAMPLE 69

1-[(1,2-Dimethyl-1H-imidazol-4-yl)sulfonyl]-3,4,5,6-tetrahydro-1H-azepino[5,4,3-cd]indole trifluoroacetate

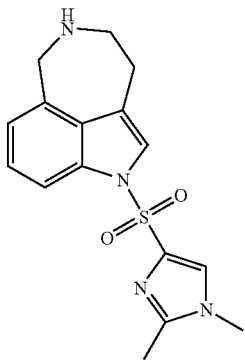

The title compound was prepared from tert-butyl 1,3,4,6-tetrahydro-5H-azepino[5,4,3-cd]indole-5-carboxylate, Intermediate 12 (14 mg, 0.05 mmol) and 1,2-dimethyl-1H-imidazole-4-sulfonyl chloride (15 mg, 0.75 mmol) as described in the general procedure above, to give 15.6 mg of product. MS (ESI) m/z 331 [M+H]$^+$.

EXAMPLE 70

2-Fluoro-5-(3,4,5,6-tetrahydro-1H-azepino[5,4,3-cd]indol-1-ylsulfonyl)benzonitrile trifluoroacetate

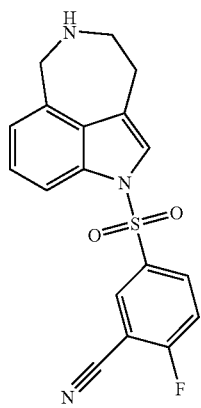

The title compound was prepared from tert-butyl 1,3,4,6-tetrahydro-5H-azepino[5,4,3-cd]indole-5-carboxylate, Intermediate 12 (14 mg, 0.05 mmol) and 3-cyano-4-fluorobenzenesulfonyl chloride (17 mg, 0.75 mmol) as described in the general procedure above, to give 14.6 mg of product. MS (ESI) m/z 356 [M+H]$^+$.

EXAMPLE 71

1-{[3-(Trifluoromethyl)phenyl]sulfonyl}-3,4,5,6-tetrahydro-1H-azepino[5,4,3-cd]indole trifluoroacetate

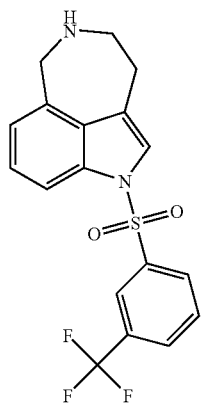

The title compound was prepared from tert-butyl 1,3,4,6-tetrahydro-5H-azepino[5,4,3-cd]indole-5-carboxylate, Intermediate 12 (14 mg, 0.05 mmol) and 3-trifluoromethylbenzenesulfonyl chloride (18 mg, 0.75 mmol) as described in the general procedure above, to give 1.7 mg of product. MS (ESI) m/z 381 [M+H$^+$].

EXAMPLE 72

6-Methyl-1-(phenylsulfonyl)-3,4,5,6-tetrahydro-1H-azepino[5,4,3-cd]indole

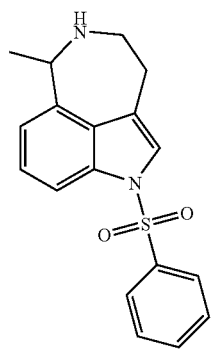

A solution of tert-butyl 6-methyl-1-(phenylsulfonyl)-7-{[(trifluoromethyl)sulfonyl]oxy}-1,3,4,6-tetrahydro-5H-azepino[5,4,3-cd]indole-5-carboxylate, Intermediate 16 (16 mg, 0.028 mmol) in MeOH (4 mL) and was carefully added to a 16 mm test tube containing Pd/C (35 mg). The suspension was purged with N$_2$, ammonium formate (88 mg, 1.4 mmol) was added in one portion, the mixture was N$_2$-purged once more and the mixture was stirred at room temperature over two days. The detriflated intermediate was purified with preparative HPLC (ACE C8 5 mm, water containing 0.1% TFA —CH$_3$CN). The pure fraction was evaporated at reduced pressure, DCM/TFA 50/50, (1 mL) was added and the mixture was left at room temperature for one hour. The crude was purified by preparative HPLC (Xterra C18, 10 mM NH$_4$CO$_3$ (pH 10)-CH$_3$CN) to give 0.8 mg of the title compound as a white oil. MS (ESI) m/z 326 [M+H]$^+$.

INTERMEDIATE 17 tert-Butyl 3-oxo-1,3,4,6-tetrahydro-5H-azepino[5,4,3-cd]indole-5-carboxylate

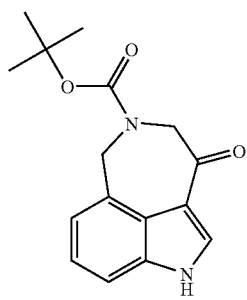

tert-butyl 1,3,4,6-tetrahydro-5H-azepino[5,4,3-cd]indole-5-carboxylate, Intermediate 12 (100 mg, 0.37 mmol) and 2,3-dichloro-5,6-dicyano-1,4-benzoquinone (DDQ) (167 mg, 0.73 mmol) in THF/water 9/1 (8 ml) was stirred under $N_2$ over night at room temperature. The compound was purified on a Biotage preparative flash column eluting with 15-100% EtOAc in petroleum ether 40-65° C. Obtained 58 mg of the title compound. MS (ESI$^+$) m/z 231 [M+H-isobutene]$^+$.

INTERMEDIATE 18 tert-Butyl 3-oxo-1-(phenylsulfonyl)-1,3,4,6-tetrahydro-5H-azepino[5,4,3-cd]indole-5-carboxylate

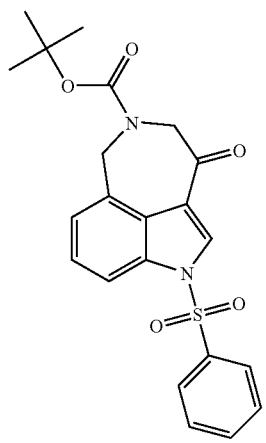

Tert-Butyl 3-oxo-1,3,4,6-tetrahydro-5H-azepino[5,4,3-cd]indole-5-carboxylate, Intermediate 17 (50 mg, 0.17 mmol), tetrabutylammonium hydrogensulfate (8 mg, 0.01 mmol) and benzenesulfonyl chloride (25 µl, 0.19 mmol) were dissolved in DCM (2 ml). 2.5 M NaOH (77 µl) was added. The mixture was stirred for 1 h at room temperature. The DCM phase was collected and washed with NaHCO$_3$(sat.) and water. Evaporation gave a residue that was purified on silica 8-66% EtOAc in petroleum ether 45-60°. Obtained 42.4 mg of the title compound as a clear glass. MS (ESI$^+$) m/z 371 [M+H-isobutene]$^+$.

EXAMPLE 73

1-(Phenylsulfonyl)-1,4,5,6-tetrahydro-3H-azepino[5,4,3-cd]indol-3-one trifluoroacetate

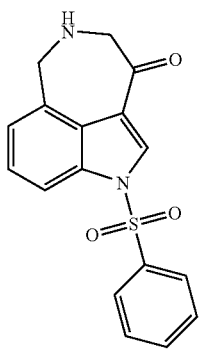

tert-Butyl 3-oxo-1-(phenylsulfonyl)-1,3,4,6-tetrahydro-5H-azepino[5,4,3-cd]indole-5-carboxylate, Intermediate 18 (5.0 mg, 0.012 mmol) was dissolved in DCM (1 ml). TFA (0.5 ml) was added and the solution was heated to boiling. The solvent was evaporated. Obtained 5.2 mg of the TFA salt. MS (ESI$^+$) m/z 327 [M+H]$^+$.

EXAMPLE 74

1-(Pyridin-3-ylsulfonyl)-3,4,5,6-tetrahydro-1H-azepino[5,4,3-cd]indole bis(trifluoroacetate)

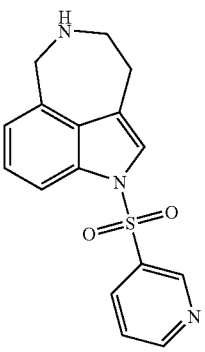

To a solution of tert-butyl 1,3,4,6-tetrahydro-5H-azepino[5,4,3-cd]indole-5-carboxylate, Intermediate 12 (25 mg, 0.092 mmol) in DCM (2 mL) were added tetrabutylammonium hydrogensulfate (6.4 mg, 0.02 mmol), 2M NaOH (0.2 mL) and pyridine-3-sulfonyl chloride*HCl (33 mg, 0.18 mmol). The reaction mixture was vigorously stirred at room temperature for one hour. More 2M NaOH (1 mL) was added to the mixture, followed by half an equivalent of the sulphonyl chloride every hour for four hours. Water (10 mL) was added and the aqueous phase was washed twice with CHCl$_3$ and the combined organic phases were evaporated at reduced pressure. To the resulting oil was added TFA/DCM 50/50 (1 mL) and the mixture was stirred at room temperature over night.

The solvent was removed at reduced pressure and the crude was purified with preparative HPLC (ACE C8 5 mm, water containing 0.1% TFA —CH$_3$CN) to give 4.6 mg of the title compound. MS (ESI) m/z 314 [M+H]$^+$.

EXAMPLE 75

1-(Phenylsulfonyl)-3,4,5,6-tetrahydro-1H-azepino[5,4,3-cd]indol-3-ol trifluoroacetate

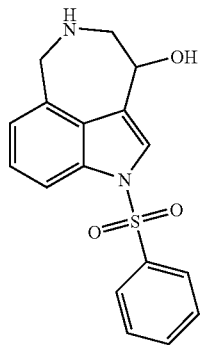

tert-Butyl 3-oxo-1-(phenylsulfonyl)-1,3,4,6-tetrahydro-5H-azepino[5,4,3-cd]indole-5-carboxylate Intermediate 18 (11 mg, 0.03 mmol) was dissolved in DCM (1 ml). TFA (0.5 ml) was added and the solution was heated to boiling, and then evaporated. The residue was dissolved in EtOH (3 ml). Sodium borohydride (7.5 mg, 0.2 mmol) was added. The reaction mixture was stirred at room temperature for 45 min. The solution was acidified with acetic acid, and evaporated. The evaporation procedure was repeated twice with the addition of methanol. The crude product was purified by preparative HPLC (ACE C8 5 mm, water containing 0.1% TFA-CH3CN) to give the title compound, 7 mg.

MS (ESI) m/z 311 [M+H—H$_2$O)$^+$ and m/z 329 [M+H]$^+$.

Biological Tests

The ability of a compound according to the invention to bind to a 5-HT$_6$ receptor, and to be pharmaceutically useful, can be determined using in vivo and in vitro assays known in the art.

(a) 5-HT$_6$ Receptor Binding Assay

Binding affinity experiment for the human 5-HT$_6$ receptor are performed in HEK293 cells transfected with 5-HT$_6$ receptor using [$^3$H]-LSD as labeled ligand according to the general method as described by Boess F. G et al. Neuropharmacology 36(4/5) 713-720, 1997.

Materials:

Cell Culture

The HEK-293 cell line transfected with the human 5-HT$_6$ receptor was cultured in Dulbeccos Modified Eagles Medium containing 5% dialyzed foetal bovine serum, (Gibco BRL 10106-169), 0.5 mM sodium pyruvate and 400 μg/ml Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England) was in ethanol and stored at −20° C. The compounds were dissolved in 100% DMSO and diluted with binding buffer.

Disposable

Compounds were diluted in Costar 96 well V-bottom polypropylene plates (Corning Inc. Costar, N.Y., USA).

Samples were incubated in Packard Optiplate (Packard Instruments B.V., Groningen, The Netherlands). The total amount of added radioligand was measured in Packard 24-well Barex plates (Packard Instruments B.V., Groningen, The Netherlands) in the presence of Microscin™20 scintillation fluid (Packard Bioscience, Meriden, Conn., USA).

Buffer

The binding buffer consisted of 20 mM HEPES, 150 mM NaCl, 10 mM MgCl$_2$, and 1 mM, EDTA, pH 7.4.

Methods:

Membrane Preparation

Cells were grown to approximately 90% confluence on 24.5×24.5 mm culture dishes. The medium was aspirated, and after rinsing with ice-cold PBS, the cells were scraped off using 25 ml Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20 000×g), suspended in binding buffer, and frozen in aliquots at −70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 ml of binding buffer per 96-well plate. The binding reaction was then initiated by adding radioligand and test compounds to the bead-membrane suspension. Following incubation at room temperature, the assay plates were subjected to scintillation counting.

The original SPA method was followed except for that membranes were prepared from HEK293 cells expressing the human 5-HT$_6$ receptor instead of from HeLa cells (Dinh D M, Zaworski P G, Gill G S, Schlachter S K, Lawson C F, Smith M W. Validation of human 5-HT$_6$ receptors expressed in HeLa cell membranes: saturation binding studies, pharmacological profiles of standard CNS agents and SPA development. (The Upjohn Company Technical Report 7295-95-064 1995; 27 December). The specific binding of [$^3$H]-LSD was saturable, while the non-specific binding increased linearly with the concentration of added radioligand. [$^3$H]-LSD bound with high affinity to 5-HT$_6$ receptors. The K$_d$ value was estimated to 2.6±0.2 nM based on four separate experiments.

The total binding at 3 nM of [$^3$H]-LSD, the radioligand concentration used in the competition experiments, was typically 6000 dpm, and the specific binding more than 70%. 5-HT caused a concentration dependent inhibition of [$^3$H]-LSD binding with an over all average Ki value of 236 nM when tested against two different membrane preparations. The inter assay variability over three experiments showed a CV of 10% with an average K$_i$ values of 173 nM (SD 30) and a Hill coefficient of 0.94 (SD 0.09). The intra assay variation was 3% (n=4). All unlabelled ligands displaced the specific binding of [$^3$H]-LSD in a concentration-dependent manner, albeit at different potencies. The rank order of affinity for the 5-HT$_6$ receptor of reference compounds was methiothepin (Ki 2 nM)>mianserin (190 nM)≈5-HT (236 nM)>methysergide (482 nM)>mesulergine (1970 nM).

Protein Determination

Protein concentrations were determined with BioRad Protein Assay (Bradford M. M. (1976) Anal. Biochem. 72:248-254). Bovine serum albumin was used as standard.

Scintillation Counting

The radioactivity was determined in a Packard Top-Count™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H]-LSD) were used in saturation experiments. The specific binding was calculated as the difference between total binding and non-specific binding, which was determined as the binding of radioligand in the presence of 5 µM lisuride. $B_{max}$ and the dissociation constant, $K_d$, were determined from the non-linear regression analysis using equation 1. $L_u$ is the unbound concentration of radioligand, and is y is the amount bound.

$$y = \frac{B_{max} \cdot Lu}{Lu + Kd} \quad \text{(equation 1)}$$

Competition Experiments

Total- and non-specific binding of radioligand was defined in eight replicates of each. Samples containing test compound were run in duplicate at 11 concentrations. Incubations were carried out at room temperature for 3 hours. The IC$_{50}$ value, i.e. the concentration of test compound that inhibited 50% of the specific binding of radioligand, was determined with non linear regression analysis and the $K_i$ value was calculated using equation 2 [Cheng Y. C. Biochem. Pharmacol. 22, 3099-3108, 1973].

$$Ki = \frac{IC_{50}}{1 + \frac{L}{K_d}} \quad \text{(equation 2)}$$

L=concentration of radioligand
$K_d$=Affinity of radioligand (b) 5-HT$_6$ Intrinsic Activity Assay Antagonists to the human 5-HT$_6$ receptor were characterized by measuring inhibition of 5-HT induced increase in cAMP in HEK 293 cells expressing the human 5-HT$_6$ receptor (see Boess et al. (1997) Neuropharmacology 36: 713-720). Briefly, HEK293/5-HT$_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% CO$_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 µl dissolved in assay medium, the cells were incubated for 10 min at +37° C. in a 5% CO$_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times EC$_{50}$) evoked increase in cAMP, using the formula IC$_{50,corr}$=IC$_{50}$/(1+[5HT]/EC$_{50}$).

The compounds in accordance with the invention have a selective affinity to human 5-HT$_6$ receptors with $K_i$ and IC$_{50,corr}$ values between 0.1 nM and 5 µM or display a % inhibition of [$^3$H]-LSD≧20% at 50 nM and are antagonists, agonists or partial agonists at the human 5-HT$_6$ receptor.

TABLE 1

Binding affinity ($K_i$) at the h5-HT$_6$ receptor

| Example | $K_i$ (nM) |
|---|---|
| 5 | 21 |
| 13 | 6 |

TABLE 2

Antagonist potency at the h5-HT$_6$ receptor

| Example | IC$_{50,corr}$ (nM) |
|---|---|
| 3 | 28 |
| 15 | 8 |

(c) In Vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473-495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57BL/6JBom; Bomholtsgaard, Denmark) 8-9 weeks with an average body weight of 50 g (obese) and 25 g (lean) are used in all the studies. The animals are housed singly in cages at 23±1° C., 40-60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulphonic acid, polyethylene glycol/methane sulphonic acid, saline. Fresh solutions are made for each study. Doses of 30, 50 and 100 mg kg$^{-1}$day$^{-1}$ are used. The purity of the test compounds is of analytical grade.

The animals are weighed at the start of the study and randomized based on body weight. Alzet osmotic minipumps (Model 2001 D; infusion rate 8 µl/h) are used and loaded essentially as recommended by the Alzet technical information manual (Alza Scientific Products, 1997; Theeuwes, F. and Yam, S. I. Ann. Biomed. Eng. 4(4). 343-353, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean ±SD and ±SEM from eight animals per dose group. Statistical evaluation is performed by Kruskal-Wallis one-way ANOVA using the percent basal values. If statistical significance is reached at the level of p<0.05, Mann-Whitney U-test for statistical comparison between control and treatment groups is performed.

The compounds according to the invention show an effect (i.e., reduction of food intake) in the range of 5-200 mg/kg/d.

The invention claimed is:

1. A compound of the Formula (I)

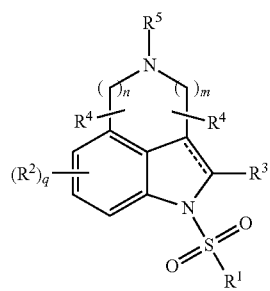

(I)

including pharmaceutically acceptable salts, geometrical isomers, tautomers, and optical isomers thereof, wherein:

⸺ represents a double bond;

m and n are each independently selected from 1 and 2, provided that m+n≦3;

$R^1$ is a group selected from:
 (a) aryl, and
 (b) heteroaryl;

wherein any heteroaryl or aryl residue, alone or as part of another group, is optionally independently substituted in one or more positions with a substituent selected from:
 (a) halogen,
 (b) $C_{1-6}$-alkyl,
 (c) hydroxy-$C_{1-6}$-alkyl,
 (d) fluoro-$C_{1-6}$-alkyl,
 (e) $C_{3-7}$-cycloalkyl,
 (f) hydroxy-$C_{3-7}$-cycloalkyl,
 (g) fluoro-$C_{3-7}$-cycloalkyl,
 (h) methyl-$C_{3-7}$-cycloalkyl,
 (i) $C_{3-4}$-cycloalkyl-$C_{1-3}$-alkyl,
 (j) $C_{3-4}$-cycloalkyl(hydroxy)-$C_{1-3}$-alkyl,
 (k) $C_{1-6}$-alkoxy,
 (l) fluoro-$C_{1-6}$-alkoxy,
 (m) $C_{1-2}$-alkoxy-$C_{1-4}$-alkyl,
 (n) $C_{3-7}$-cycloalkoxy,
 (o) fluoro-$C_{3-7}$-cycloalkoxy,
 (p) methyl-$C_{3-7}$-cycloalkoxy,
 (q) $C_{2-6}$-alkenyl,
 (r) fluoro-$C_{2-6}$-alkenyl,
 (s) $C_{2-6}$-alkynyl,
 (t) hydroxy,
 (u) —$SCF_3$,
 (v) —$SCF_2H$,
 (w) —$SO_2NR^6R^6$,
 (x) —$S(O)_eR^7$, wherein e is 0, 1, 2 or 3,
 (y) —$OSO_2R^7$,
 (z) —CN,
 (aa) —$NR^6R^6$,
 (ab) —$NHSO_2R^7$,
 (ac) —$NR^8COR^7$,
 (ad) —$NO_2$,
 (ae) —$CONR^6R^6$,
 (af) —CO—$R^7$,
 (ag) —COOH,
 (ah) $C_{1-6}$-alkoxycarbonyl,
 (ai) aryl,
 (aj) heteroaryl,
 (ak) aryloxy, and
 (al) heteroaryloxy;

wherein any (ai) aryl or (aj) heteroaryl, alone or as part of another group, is optionally substituted in one or more positions with a substituent selected from:
 (a) halogen,
 (b) $C_{1-4}$-alkyl,
 (c) $C_{1-4}$-alkoxy,
 (d) —$CF_3$, and
 (e) —CN;

q is selected from 0, 1 and 2;

each $R^2$ is independently selected from:
 (a) $C_{1-6}$-alkoxy,
 (b) hydroxy, and
 (c) —$OSO_2$—$CF_3$, $R^3$ is hydrogen;

each $R^4$ is independently selected from:
 (a) hydrogen,
 (b) $C_{1-4}$-alkyl,
 (c) hydroxy, and
 (d) oxo,
 provided that when $R^4$ is hydroxy or oxo, then either m or n is 2, and $R^4$ is
 not attached on a carbon in alpha position to the ring nitrogen atom;

$R^5$ is a group selected from:
 (a) hydrogen, and
 (b) $C_{1-4}$-alkyl, each $R^6$ is a group independently selected from:
 (a) hydrogen,
 (b) $C_{1-6}$-alkyl,
 (c) fluoro-$C_{2-6}$-alkyl, and
 (d) $C_{3-7}$-cycloalkyl, or
 two $R^6$ groups together with the nitrogen to which they are attached form a heterocyclic ring optionally substituted with methyl;

each $R^7$ is a group independently selected from:
 (a) hydrogen,
 (b) $C_{1-6}$-alkyl,
 (c) fluoro-$C_{1-6}$-alkyl,
 (d) $C_{3-7}$-cycloalkyl,
 (e) methyl-$C_{3-7}$-cycloalkyl,
 (f) $C_{3-4}$-cycloalkyl-$C_{1-3}$-alkyl,
 (g) aryl, and
 (h) heteroaryl;

wherein any heteroaryl or aryl residue is optionally independently substituted in one or more positions with a substituent selected from:
 (a) halogen,
 (b) $C_{1-4}$-alkyl, (c) C$_{1-4}$-alkoxy,
(d) —CF$_3$, and
(e) —CN;
each R$^8$ is independently a group selected from:
(a) hydrogen,
(b) C$_{1-6}$-alkyl,
(c) fluoro-C$_{1-6}$-alkyl, and
(d) C$_{3-7}$-cycloalkyl,
or R$^7$ and R$^8$ together with the atoms to which they are attached form a lactam ring when present in the group NR$^8$COR$^7$, or R$^7$ and R$^8$ together with the atoms to which they are attached form a sultam ring when present in the group NR$^8$SO$_2$R$^7$;
provided that the said compound of Formula (I) is not 1-[(4-methylphenyl)sulfonyl]-3,4,5,6-tetrahydro-1H-azepino[5,4,3-cd]indole.

2. A compound of claim 1, wherein R$^1$ is a group selected from:
(a) aryl, and
(b) heteroaryl,
wherein any heteroaryl or aryl residue is optionally independently substituted in one or more positions with a substituent selected from:
(a) halogen,
(b) C$_{1-6}$-alkyl,
(c) fluoro-C$_{1-6}$-alkyl,
(d) C$_{1-6}$-alkoxy,
(e) fluoro-C$_{1-6}$-alkoxy, and
(f) —CN.

3. A compound according to claim 2 wherein any heteroaryl or aryl residue is optionally independently substituted in one or more positions with a substituent selected from:
(a) halogen,
(b) C$_{1-4}$-alkyl,
(c) fluoro-C$_{1-2}$-alkyl,
(d) C$_{1-2}$-alkoxy,
(e) fluoro-C$_{1-2}$-alkoxy, and
(f) —CN.

4. A compound of claim 3 wherein q is 0.

5. A compound of claim 1 wherein q is 1 or 2, and each R$^2$ is independently a group selected from:
(a) C$_{1-2}$-alkoxy,
(b) hydroxy, and
(c) —O—SO$_2$—CF$_3$.

6. A compound of claim 1 wherein R$^5$ is a group selected from:
(a) hydrogen,
(b) C$_{1-3}$-alkyl,
(c) N(R$^6$)$_2$-C$_{2-4}$-alkyl-,
(d) imidazolyl-methyl, and
(e) pyrrolidinyl-methyl.

7. A compound of claim 1 wherein each R$^6$ independently is a group selected from:
(a) hydrogen, and
(b) methyl.

8. A compound of claim 1 wherein m+n=3.

9. A compound according to claim 8 wherein:
R$^1$ is a group selected from:
(a) phenyl,
(b) furanyl,
(c) thienyl,
(d) isoxazolyl,
(e) imidazolyl,
(f) thiazolyl,
(g) pyridyl,
(h) imidazothiazolyl,
(i) benzofuranyl,
(j) dihydrobenzofuranyl,
(k) benzothienyl, and
(l) benzothiazolyl,
wherein R$^1$ is unsubstituted or independently substituted in one or more positions with a substituent selected from:
(a) fluoro,
(b) chloro,
(c) bromo,
(d) methyl,
(e) ethyl,
(f) n-propyl,
(g) isopropyl,
(h) tert-butyl,
(i) trifluoromethyl,
(j) methoxy,
(k) ethoxy, and
(l) cyano;
q is 0 or 1;
each R$^2$ is independently a group selected from
(a) methoxy,
(b) ethoxy,
(c) hydroxy, and
(d) —O—SO$_2$—CF$_3$;
R$^3$ is hydrogen;
each R$^4$ is independently a group selected from
(a) hydrogen,
(b) methyl, and
(c) oxo
wherein at least one R$^4$ is hydrogen; and
R$^5$ is a group selected from:
(a) hydrogen,
(b) methyl, and
(c) ethyl.

10. A compound according to claim 9, which is selected from:
4-methyl-1-(phenylsulfonyl)-3,4,5,6-tetrahydro-1H-azepino[3,4,5-cd]indole,
4-ethyl-1-(phenylsulfonyl)-3,4,5,6-tetrahydro-1H-azepino[3,4,5-cd]indole,
1-(phenylsulfonyl)-3,4,5,6-tetrahydro-1H-azepino[5,4,3-cd]indole,
5-methyl-1-(phenylsulfonyl)-3,4,5,6-tetrahydro-1H-azepino[5,4,3-cd]indole,
1-(phenylsulfonyl)-3,4,5,6-tetrahydro-1H-azepino[3,4,5-cd]indole,
7-methoxy-6-methyl-1-(phenylsulfonyl)-3,4,5,6-tetrahydro-1H-azepino[5,4,3-cd]indole,
6-methyl-1-(phenylsulfonyl)-3,4,5,6-tetrahydro-1H-azepino[5,4,3-cd]indol-7-ol,
6-methyl-1-(phenylsulfonyl)-3,4,5,6-tetrahydro-1H-azepino[5,4,3-cd]indol-7-yl trifluoromethanesulfonate,
7-methoxy-5,6-dimethyl-1-(phenylsulfonyl)-3,4,5,6-tetrahydro-1H-azepino[5,4,3-cd]indole,
7-ethoxy-6-methyl-1-(phenylsulfonyl)-3,4,5,6-tetrahydro-1H-azepino[5,4,3-cd]indole,
1-[(2-chloro-6-methylphenyl)sulfonyl]-3,4,5,6-tetrahydro-1H-azepino[5,4,3-cd]indole,
1-[(3-chloro-2-methylphenyl)sulfonyl]-3,4,5,6-tetrahydro-1H-azepino[5,4,3-cd]indole,
1-[(3-chloro-4-fluorophenyl)sulfonyl]-3,4,5,6-tetrahydro-1H-azepino[5,4,3-cd]indole,
1-[(2-chlorophenyl)sulfonyl]-3,4,5,6-tetrahydro-1H-azepino[5,4,3-cd]indole,
1-[(3-chlorophenyl)sulfonyl]-3,4,5,6-tetrahydro-1H-azepino[5,4,3-cd]indole,
1-[(4-chlorophenyl)sulfonyl]-3,4,5,6-tetrahydro-1H-azepino[5,4,3-cd]indole, 1-[(3-fluorophenyl)sulfonyl]-3,4,5,6-tetrahydro-1H-azepino[5,4,3-cd]indole,
1-[(4-fluorophenyl)sulfonyl]-3,4,5,6-tetrahydro-1H-azepino[5,4,3-cd]indole,
1-[(2,6-difluorophenyl)sulfonyl]-3,4,5,6-tetrahydro-1H-azepino[5,4,3-cd]indole,
1-[(2,5-difluorophenyl)sulfonyl]-3,4,5,6-tetrahydro-1H-azepino[5,4,3-cd]indole,
1-[(3,5-difluorophenyl)sulfonyl]-3,4,5,6-tetrahydro-1H-azepino[5,4,3-cd]indole,
1-[(2,4-difluorophenyl)sulfonyl]-3,4,5,6-tetrahydro-1H-azepino[5,4,3-cd]indole,
1-[(3,4-difluorophenyl)sulfonyl]-3,4,5,6-tetrahydro-1H-azepino[5,4,3-cd]indole,
1-[(2-methylphenyl)sulfonyl]-3,4,5,6-tetrahydro-1H-azepino[5,4,3-cd]indole,
1-[(2,5-dimethyl-3-thienyl)sulfonyl]-3,4,5,6-tetrahydro-1H-azepino[5,4,3-cd]indole,
1-[(2,5-dimethylphenyl)sulfonyl]-3,4,5,6-tetrahydro-1H-azepino[5,4,3-cd]indole,
1-[(3,5-dimethylphenyl)sulfonyl]-3,4,5,6-tetrahydro-1H-azepino[5,4,3-cd]indole,
1-{[4-fluoro-3-(trifluoromethyl)phenyl]sulfonyl}-3,4,5,6-tetrahydro-1H-azepino[5,4,3-cd]indole,
1-(1-benzofuran-2-ylsulfonyl)-3,4,5,6-tetrahydro-1H-azepino[5,4,3-cd]indole,
1-(1,3-benzothiazol-6-ylsulfonyl)-3,4,5,6-tetrahydro-1H-azepino[5,4,3-cd]indole,
1-[(1-methyl-1H-imidazol-4-yl)sulfonyl]-3,4,5,6-tetrahydro-1H-azepino[5,4,3-cd]indole,
1-[(6-chloroimidazo[2,1-b][1,3]thiazol-5-yl)sulfonyl]-3,4,5,6-tetrahydro-1H-azepino[5,4,3-cd]indole,
1-{[2-(trifluoromethyl)phenyl]sulfonyl}-3,4,5,6-tetrahydro-1H-azepino[5,4,3-cd]indole,
1-(1-benzothien-2-ylsulfonyl)-3,4,5,6-tetrahydro-1H-azepino[5,4,3-cd]indole,
1-[(5-fluoro-2-methylphenyl)sulfonyl]-3,4,5,6-tetrahydro-1H-azepino[5,4,3-cd]indole,
1-{[3-(trifluoromethyl)phenyl]sulfonyl}-3,4,5,6-tetrahydro-1H-azepino[5,4,3-cd]indole,
1-{[4-(trifluoromethyl)phenyl]sulfonyl}-3,4,5,6-tetrahydro-1H-azepino[5,4,3-cd]indole,
4-methyl-2-(3,4,5,6-tetrahydro-1H-azepino[5,4,3-cd]indol-1-ylsulfonyl)benzonitrile,
1-[(4,5-dichloro-2-thienyl)sulfonyl]-3,4,5,6-tetrahydro-1H-azepino[5,4,3-cd]indole,
1-[(4-tert-butylphenyl)sulfonyl]-3,4,5,6-tetrahydro-1H-azepino[5,4,3-cd]indole,
1-[(2,5-dimethyl-3-furyl)sulfonyl]-3,4,5,6-tetrahydro-1H-azepino[5,4,3-cd]indole,
1-[(2,4-dimethyl-1,3-thiazol-5-yl)sulfonyl]-3,4,5,6-tetrahydro-1H-azepino[5,4,3-cd]indole,
1-[(3,5-dimethylisoxazol-4-yl)sulfonyl]-3,4,5,6-tetrahydro-1H-azepino[5,4,3-cd]indole,
1-[(5-chloro-2-thienyl)sulfonyl]-3,4,5,6-tetrahydro-1H-azepino[5,4,3-cd]indole,
4-(3,4,5,6-tetrahydro-1H-azepino[5,4,3-cd]indol-1-ylsulfonyl)benzonitrile,
3-(3,4,5,6-tetrahydro-1H-azepino[5,4,3-cd]indol-1-ylsulfonyl)benzonitrile,
1-[(4-methoxyphenyl)sulfonyl]-3,4,5,6-tetrahydro-1H-azepino[5,4,3-cd]indole,
1-[(2-methoxy-6-methylphenyl)sulfonyl]-3,4,5,6-tetrahydro-1H-azepino[5,4,3-cd]indole,
1-[(2-methoxy-5-methylphenyl)sulfonyl]-3,4,5,6-tetrahydro-1H-azepino[5,4,3-cd]indole,
1-[(2-methoxy-4-methylphenyl)sulfonyl]-3,4,5,6-tetrahydro-1H-azepino[5,4,3-cd]indole,
1-(1-benzothien-3-ylsulfonyl)-3,4,5,6-tetrahydro-1H-azepino[5,4,3-cd]indole,
1-[(4-isopropylphenyl)sulfonyl]-3,4,5,6-tetrahydro-1H-azepino[5,4,3-cd]indole,
1-[(4-propylphenyl)sulfonyl]-3,4,5,6-tetrahydro-1H-azepino[5,4,3-cd]indole,
1-[(5-ethyl-2-methoxyphenyl)sulfonyl]-3,4,5,6-tetrahydro-1H-azepino[5,4,3-cd]indole,
1-[(5-bromo-2,3-dihydro-1-benzofuran-7-yl)sulfonyl]-3,4,5,6-tetrahydro-1H-azepino[5,4,3-cd]indole,
1-[(5-chloro-3-methyl-1-benzothien-2-yl)sulfonyl]-3,4,5,6-tetrahydro-1H-azepino[5,4,3-cd]indole,
1-[(2-ethoxy-5-isopropylphenyl)sulfonyl]-3,4,5,6-tetrahydro-1H-azepino[5,4,3-cd]indole,
6-methyl-1-(phenylsulfonyl)-3,4,5,6-tetrahydro-1H-azepino[5,4,3-cd]indole,
1-(phenylsulfonyl)-1,4,5,6-tetrahydro-3H-azepino[5,4,3-cd]indol-3-one,
1-[(1,2-dimethyl-1H-imidazol-4-yl)sulfonyl]-3,4,5,6-tetrahydro-1H-azepino[5,4,3-cd]indole,
2-fluoro-5-(3,4,5,6-tetrahydro-1H-azepino[5,4,3-cd]indol-1-ylsulfonyl)benzonitrile,
1-(pyridin-3-ylsulfonyl)-3,4,5,6-tetrahydro-1H-azepino[5,4,3-cd]indole, and
1-(phenylsulfonyl)-3,4,5,6-tetrahydro-1H-azepino[5,4,3-cd]indol-3-ol.

11. A compound of claim 1 which is a 5-HT$_6$ receptor antagonist or partial agonist.

12. A compound according to claim 11 which is a 5-HT$_6$ receptor antagonist.

13. A method for modulating 5-HT$_6$ receptor activity, comprising administering to a mammal an effective amount of a compound of claim 1.

14. A pharmaceutical formulation containing a compound of claim 11 as active ingredient in combination with a pharmaceutically acceptable diluent or carrier.

15. A pharmaceutical composition containing a compound of claim 9 as active ingredient in combination with a pharmaceutically acceptable diluent or carrier.

16. A pharmaceutical composition containing a compound of claim 10 as active ingredient in combination with a pharmaceutically acceptable diluent or carrier.

17. A pharmaceutical composition containing as active ingredient a compound selected from 1-[(3,5-dimethylphenyl)sulfonyl]-3,4,5,6-tetrahydro-1H-azepino[5,4,3-cd]indole, 1-{[3-(trifluoromethyl)phenyl]sulfonyl}-3,4,5,6-tetrahydro-1H-azepino[5,4,3-cd]indole, and pharmaceutically acceptable salts thereof,
in combination with a pharmaceutically acceptable diluent or carrier.

* * * * *